US008449867B2

(12) United States Patent
Larm et al.

(10) Patent No.: US 8,449,867 B2
(45) Date of Patent: May 28, 2013

(54) MICROEMULSION AND SUB-MICRON EMULSION PROCESS AND COMPOSITIONS

(75) Inventors: Maria Graziella Larm, Rosanna (AU); Ronald Harding, North Warrandyte (AU); Michael Johnston, Yarraville (AU); Albert Zorko Abram, Wantirna (AU); Prema Vijayakumar, Fremont, CA (US); Phoebe Sun, Mountain View, CA (US)

(73) Assignee: Stiefel Research Australia Pty Ltd, Rowville (AU)

( * ) Notice: Subject to any disclaimer, the term of this patent is extended or adjusted under 35 U.S.C. 154(b) by 589 days.

(21) Appl. No.: 12/457,953

(22) Filed: Jun. 25, 2009

(65) Prior Publication Data
US 2010/0055137 A1    Mar. 4, 2010

Related U.S. Application Data

(63) Continuation-in-part of application No. 11/216,668, filed on Aug. 31, 2005.

(60) Provisional application No. 60/670,722, filed on Apr. 12, 2005, provisional application No. 60/606,278, filed on Aug. 31, 2004.

(51) Int. Cl.
*A61K 9/00* (2006.01)
*A61K 8/02* (2006.01)
*A61K 8/00* (2006.01)
*A61K 31/59* (2006.01)
*A61K 31/56* (2006.01)
*A01N 45/00* (2006.01)

(52) U.S. Cl.
USPC ......... 424/47; 424/401; 424/400; 514/167; 514/168; 514/169; 514/937; 514/178

(58) Field of Classification Search
USPC ............... 424/400, 401, 47; 514/167, 168, 514/169, 937, 178
See application file for complete search history.

(56) References Cited

U.S. PATENT DOCUMENTS

| | | | |
|---|---|---|---|
| 3,641,181 A | 2/1972 | Robbins et al. | |
| 4,146,499 A * | 3/1979 | Rosano | 252/186.32 |
| 4,655,959 A | 4/1987 | Stopper | |
| 4,820,820 A | 4/1989 | Sebag et al. | |
| 5,362,494 A | 11/1994 | Zysman et al. | |
| 5,474,776 A | 12/1995 | Koyanagi et al. | |
| 5,591,449 A | 1/1997 | Bollens et al. | |
| 5,665,700 A | 9/1997 | Cho et al. | |
| 5,853,711 A | 12/1998 | Nakamura et al. | |
| 6,413,527 B1 | 7/2002 | Simonnet et al. | |
| 6,455,066 B1 | 9/2002 | Fischer et al. | |
| 6,464,990 B2 | 10/2002 | Simonnet et al. | |
| 6,902,737 B2 | 6/2005 | Quemin | |
| 7,357,922 B1 | 4/2008 | Brock et al. | |
| 2001/0055597 A1 * | 12/2001 | Liu et al. | 424/400 |
| 2002/0146375 A1 | 10/2002 | Schreiber et al. | |
| 2002/0193831 A1 | 12/2002 | Smith, III | |
| 2003/0083314 A1 | 5/2003 | Yiv et al. | |
| 2003/0087967 A1 | 5/2003 | Quemin | |
| 2003/0171479 A1 * | 9/2003 | Lennon | 524/501 |
| 2003/0232091 A1 * | 12/2003 | Shefer et al. | 424/490 |

FOREIGN PATENT DOCUMENTS

| | | |
|---|---|---|
| CA | 2 503 539 A1 | 5/2004 |
| DE | 195 09 079 A1 | 9/1996 |
| EP | 0 696 452 A1 | 2/1996 |
| EP | 0 875 244 A2 | 11/1998 |
| EP | 1 018 363 A1 | 7/2000 |
| EP | 1 020 219 A1 | 7/2000 |
| JP | 11-501641 A | 2/1999 |
| JP | 2000-212030 A | 8/2000 |
| WO | 93/15018 A1 | 8/1993 |
| WO | WO 99/44585 A1 | 9/1999 |
| WO | 01/20990 A1 | 3/2001 |
| WO | 02/056843 A2 | 7/2002 |

OTHER PUBLICATIONS

Extended European Search Report, received on Jan. 28, 2011, for European Application No. 05775966.4, nine pages.
Morrison, *Cosmetics and Toiletries*, 1996, 11(1), pp. 59-65.
Förster et al. "Phase Inversion Emulsification" *Cosmetics and Toiletries*, Dec. 1991, vol. 106, pp. 49-52.
MeSH Descriptor Data, http://www.nlm.nih.gov/mesh/MBrowser.html, last updated Oct. 15, 2008.
Ghebremeskel et al., International Journal of Pharmaceutics, 2007, 328, 119-129.
Derwent Abstract Accession No. 86-205112, Class B07, DD-234611-A (Luther-Univ Halle) Apr. 9, 1986.
Derwent Abstract Accession No. 86-205113, Class B07, DD-234612-A (Luther-Univ Halle) Apr. 9, 1986.

* cited by examiner

Primary Examiner — Abigail Fisher
(74) Attorney, Agent, or Firm — Nath, Goldberg & Meyer; Joshua B. Goldberg; Tanya E. Harkins

(57) ABSTRACT

An oil in water microemulsion or sub-micron emulsion composition for dermal delivery of at least one pharmaceutically active ingredient, is provided. The composition includes an oil phase dispersed throughout a water phase, the oil phase including at least one member selected from the group consisting of an animal oil, a mineral oil, a vegetable oil, a silane member, a siloxane, an ester, a fatty acid, a fat, a halogen compound, and an alkoxylated alcohol; and at least one lipophilic surfactant, the water phase including at least one hydrophilic surfactant, water and optionally a non-surfactant amphiphilic compound, the weight ratio of the at least one hydrophilic surfactant to the at least one lipophilic surfactant being approximately 9.0:1.0 to 2.0:3.0.

14 Claims, 11 Drawing Sheets

Ethanol-Free Clobetasol Propionate Foam, 0.05% Process Flow Diagram

FIGURE 5   BMV E - Particle Size Distribution vs Surfactant Ratio

0.2% and 10% Lactic Acid Foam Process Flow Diagram

1% Pramoxine SME Emollient Foam Process Flow Diagram

Foam Quality for Formulation 692-15-21 (Unpreserved 1% Pramoxine HCl SME Foam)

Foam Quality for Formulation 692-15-24 (Preserved 1% Pramoxine HCl SME Foam)

MICROEMULSION AND SUB-MICRON EMULSION PROCESS AND COMPOSITIONS

CROSS-REFERENCE TO RELATED APPLICATIONS

This application is a continuation-in-part of U.S. patent application Ser. No. 11/216,668, filed Aug. 31, 2005, which claims priority to U.S. Provisional Patent Application Ser. No. 60/606,278, filed Aug. 31, 2004 and U.S. Provisional Patent Application Ser. No. 60/670,722, filed Apr. 12, 2005, the contents of which are both hereby expressly incorporated by reference in their entirety.

FIELD OF THE INVENTION

This invention relates to a method of formulation of microemulsions and sub-micron emulsions useful in cosmetic and therapeutic applications in the field of dermatology. In particular, the invention relates to methods of formulation of stable microemulsions and sub-micron emulsions which may contain ingredients which are known to be disruptive of the physical state of the formulation. The invention also relates to cosmetic and therapeutic microemulsion and sub-micron emulsion compositions arising from these methods. Methods of cosmetic and therapeutic treatment using the microemulsions and sub-micron emulsions are encompassed by this invention as are the uses of the compositions arising from the formulation method in appropriate treatments.

BACKGROUND

The size of a particle is critical to its ability to cross the skin barrier and therefore its ability to deliver a pharmaceutically active ingredient for the treatment of local or systemic medical conditions of the patient concerned. As particles become smaller (particularly below 100 nm), the percentage of exposed surface area of a particle in proportion to its total volume when compared to unrefined material is increased, and hence its potential efficacy is increased.

The characteristics of sub-micron particles in their application to the delivery of pharmaceutically active ingredients across the skin barrier may be summarised as follows:

| Particle size | Description | Characteristics |
|---|---|---|
| 300-1000 nm | Emulsion | Blue-white, milky liquid, reasonable physical stability. Particles reside on skin surface → transdermal delivery. |
| 100-300 nm | Sub-micron Emulsion | Bluish, translucent liquid. Enhanced physical stability. Particles reside on skin surface → enhanced transdermal delivery. |
| 10-100 nm | Microemulsion | Translucent-transparent liquid. Excellent physical stability. Particles reside on skin surface → enhanced transdermal delivery. |
| <5 nm | Nanoparticles/ Nano-dispersion/ Micelles | Translucent-transparent liquid. Excellent physical stability. Particles reside on skin surface, within stratum corneum and in hair follicles → optimal transdermal delivery. |

Because of the desirable characteristics of so called microemulsions, and sub-micron emulsions, attempts have been made to perfect the means of their manufacture. Essentially, the much higher ratio of emulsifier to disperse phase is that feature which differentiates a microemulsion from a macroemulsion. The aim is to stabilise oil phases in water phases, or vice versa. The nature of the emulsifier (or surfactant) used is clearly very important. Oil in water micro emulsions are particularly difficult to formulate and, generally speaking, simply adapting the mode, or means of homogenization, or increasing the amount of emulsifier present will not guarantee the product is a microemulsion. The choice of emulsifier is reportedly critical to the success of the formulation (BK: MicroEmulsions Theory and Practice, Prince, Leon (ed) pp 33-50, Academic Press, NY, USA, 1977).

Water in oil systems are made by blending the oil and emulsifier, with a little heat if necessary, and then adding water. The amount of water that can be added to a given system of emulsifier and oil may not always be high enough for the application in mind. In that event, it becomes necessary to try other emulsifiers. When one is found that permits the desired water uptake, it may be convenient from a processing viewpoint to add the mixture of emulsifier and oil to the water. Again, warming the system may hasten the mixing process. In systems of oil, water and emulsifier that are capable of forming microemulsions, the order of mixing does not affect the end result.

The simplest way to make an oil in water microemulsion is to blend the oil and emulsifier and then pour this liquid mixture into the water with mild stirring. Another technique is to make a crude macroemulsion of the oil and one of the emulsifiers, for example, a soap. By using low volumes of water a gel is formed. This gel is then changed into a clear solution by titration with a second surface active agent like an alcohol. This system may then be transformed into an opalescent oil in water microemulsion of the desired concentration by further addition of water. By far the most common method of making an oil in water microemulsion, especially in the trial and error stage, however, is by the so-called inversion process.

In actual practice, oils which are capable of being microemulsified, i.e. "emulsifiable oils", as opposed to those which may be dispersed in micellar solution, invert by the slow addition of water from a fluid water in oil dispersion through a viscoelastic gel stage to a fluid oil in water microemulsion. 100% emulsifier on the weight of the oil may be employed. After careful blending, with heat if necessary, water is added to the blend in a beaker. This is done in successive, small aliquots. If the chemistry is right, a clear, transparent water in oil dispersion first forms. This is fluid. As more water is added, at about equal volumes of water and oil/emulsifier blend, the system begins to become more viscous. As more water is added, it becomes very viscous, ultimately becoming a heavy gel. At this point it is frequently helpful to apply heat to thin the gel and facilitate passage through this stage. With the addition of more water, the gel eventually thins out to a fluid oil in water microemulsion which can readily be identified by its clarity or opalescence.

The highly viscous intermediate gel stages are not microemulsions but are sometimes so called, as in the case of ringing gels used as hair pomades. These systems are actually liquid crystalline phases and occur because of the particular sequence of mixing employed in forming the microemulsion.

Given the importance of the emulsifier to the successful formulation of the microemulsion, systems have been developed to assist in selection of the emulsifier. One such system (Shiroda, K., J. Colloid Interface Sci, 24, 4 (1967)) is that based upon the temperature at which an emulsifier causes an oil in water emulsion to invert to a water in oil emulsion. It is known as the Phase Inversion Temperature (PIT) System. It provides information about various oils, phase volume relationships, and the concentration of emulsifier required. The system is established on the proposition that the hydrophilic lipophilic balance (the "HLB") of a non-ionic surfactant changes with temperature and that the inversion of emulsion type occurs when the hydrophilic and lipophilic tendencies of the emulsifier just balance each other. No emulsion forms at this temperature. Emulsions stabilised with non-ionic agents are oil in water types at low temperature and invert to water in oil types at elevated temperature. It goes without saying that use of more than one emulsifier in a composition may positively influence the formulation of a microemulsion. PIT techniques require a significant input of energy in order to attain a sub-micron emulsion. The process requires high temperature so as to render the ethoxylated surfactant hydrophobic, whereby the oil in water emulsion becomes a water in oil emulsion, and thereafter, the conversion of the water in oil dispersion to a oil in water dispersion is effected upon subsequent cooling of the formulation. At least because of the degradative effect that heat has upon certain active ingredients, it would be desirable to reduce the energy requirements for such processes as this is likely to reduce the risk of crystallisation of poorly soluble active ingredients occurring upon normal temperature cycling of the stored product Microemulsion technology has been the subject of relatively intense investigation since the late 1950's when hair gels using the technology were first developed.

One patent U.S. Pat. No. 6,333,362 (L'OREAL) describes an ultrafine foaming oil in water emulsion where the particle size of the oil particles constituting the oil phase range from 50-1000 nm. The PIT technique is used to manufacture the formulation. Example 1 describes a prior art formulation as follows:

| | % |
|---|---|
| Phase 1 | |
| dicapryl ether | 7.7 |
| Isocetyl stearate | 3.0 |
| cetearyl isononanoate | 4.0 |
| beheneth-9 | 4.5 |
| Phase 2 | |
| Distilled water | 14.7 |
| Preservative | q.s |
| Phase 3 | |
| distilled water | q.s. 100 |
| sodium lauryl ether sulphate | 5.0 | where the sodium lauryl ether sulphate in phase 3 acts as the foaming agent on dispensing the product from its pressurised can. To prepare the formulation phases 1 and 2 were heated separately to 60° C. and homogenised. Phase 2 was poured slowly, with stirring, onto Phase 1 and the mixture was heated as far as the phase inversion temperature, which was around 85° C. The heating was stopped and Phase 3 was poured in unheated and the mixture was allowed to cool while slow stirring was maintained.

Nanoemulsions which contain an amphiphilic lipid phase composed of phospholipids, water and oil are known in the art. These emulsions exhibit the disadvantage of being unstable on storage at conventional storage temperatures, namely between 0 and 45° C. They lead to yellow compositions and produce rancid smells which develop several days after storage. One example of such an emulsion is described in WO 03/08222 (BEIERDORF AG)

In practice there are challenges in formulating microemulsions. The point at which the composition inverts from an oil in water or water in oil formulation, respectively, to a water in oil or oil in water formulation, known as the "set point" needs to be carefully monitored. If the set point is not reached before the product is poured out, inversion will not occur, and so a microemulsion will not be achieved. High set points in particular can be difficult to achieve and maintain. Additives can be used to lower the set point but these can also have the effect of destabilising the microemulsion resulting in undesirable alteration of the viscosity of the microemulsion, cloudiness, and can also cause loss of invertible character altogether. Furthermore, although high levels of emulsifier can be desirable, on the other hand, high emulsifier content can lead to skin and eye irritation of the user.

Petrolatum, which is desirably used in dermatological compositions for its occlusive and emollient properties, is considered too difficult to incorporate in microemulsion formulations because of its viscosity.

Another ingredient which is desirable in dermatological applications is propylene glycol for its capacity as a penetration enhancer. However, it has been reported as undesirable in microemulsion technology because of its potential to disrupt or destabilise the formulation. WO 94/08603 (SMITHKLINE BEECHAM CORPORATION) teaches the avoidance of propylene glycol and other polyhydroxyl alcohol cosurfactants because of the processing and stability issues they introduce.

Another challenge in the application of microemulsions to the field of dermatology is the solubilisation of the pharmaceutically active ingredients in the formulations. Some pharmaceutically active ingredients are highly water soluble, or in the alternative are highly oil soluble. Others are sparingly soluble. A pharmaceutically active ingredient in solution provides better penetration than one in suspension and, both of these provide better penetration than a drug as a solid. In the case where a pharmaceutically active ingredient is not easily solubilised, the need for an additive such as propylene glycol which can assist in penetration, is obvious, but conversely the ease of formation of a microemulsion is diminished.

In light of the foregoing, it is an object of this invention to identify methods of formulating microemulsions and sub-micron emulsion formulations which may act as a vehicle for the delivery of a pharmaceutically active ingredient across the skin barrier for cosmetic or therapeutic purposes. It is a secondary object to achieve a means of incorporating one or more microemulsion disrupting substances, such as petrolatum and/or propylene glycol into such a microemulsion or sub-micron emulsion at the same time maintaining the viscosity, appearance, stability and efficacy of the formulation.

Any discussion of documents, devices, acts or knowledge in this specification is included to explain the context of the invention. It should not be taken as admission that any of the information formed part of the prior art base or the common general knowledge in the relevant art on or before the priority date of the present subject matter.

SUMMARY OF INVENTION

The present invention provides a process for the preparation of an oil in water (O/W) microemulsion or sub-micron emulsion composition for dermal delivery of at least one pharmaceutically active ingredient, the method including the steps of a) admixing a first part including at least one selected from the group consisting of animal, mineral or vegetable oils, silanes, siloxanes, esters, fatty acids, fats, halogen compounds and alkoxylated alcohols; and one or more lipophilic surfactants, and a second part including water and at least one hydrophilic surfactant to achieve homogeneity, b) heating the mix of step a) to a phase assembly temperature in the range of 40-99° C., preferably 45-95° C., more preferably 65-85° C. with continuous mixing to obtain an oil in water microemulsion or sub-micron emulsion, c) allowing said microemulsion or sub-micron emulsion to cool, and d) adding a third part to said microemulsion or sub-micron emulsion at a temperature between 2° C. and said phase assembly temperature, said third part if necessary being premixed and heated until the components are dissolved and including at least one component selected from the group consisting of non-surfactant amphiphilic type compound, surfactant and water.

This method, in one preferred embodiment of the present invention, can be achieved in such a way that the first and the second part are respectively preheated to a temperature of 40-99° C., preferably 45-95° C., and more preferably 65-85° C. and then admixed to homogeneity; and subsequently the second part is added to the first part at a temperature of 40-99° C., preferably 45-95° C., and more preferably 65-85° C. with continuous mixing whereby a microemulsion or sub-micron emulsion is formed at a phase assembly temperature.

The phase assembly temperature can be determined visually by the achievement of translucence in the composition or by measures such as conductivity which peaks and then is maintained at a plateau whilst phase assembly occurs.

It has been found that where a non-surfactant amphiphilic type compound such as the polyol is added, if such a compound added together with the second part as would conventionally be the case, a microemulsion or sub-micron emulsion is not formed. However, by adding the so called third part, phase assembly occurs at a lower temperature than would be expected and moreover, this phase appears to assist in maintaining the microemulsion or sub-micron emulsion characteristics of the formulation during storage at normal temperatures. This is a particularly useful phenomenon where it is desirable to use pharmaceutically active ingredients which tend towards insolubility except in solvents including a polyol and/or alcohol. By effectively lowering the temperature at which phase assembly is achieved, active ingredients which are degraded by exposure to temperature are more preserved than is the case in prior art formulations. It is thus believed that the shelf life of the formulations according to the present invention can be prolonged as compared to prior art compositions.

The water phase of the microemulsion or sub-micron emulsion is desirably added in two aliquots, ⅔ and ⅓; in aliquots more preferably of about 70-80% and 20-30% by weight of the total water phase. More preferably still, the second aliquot is added after the microemulsion or sub-micron emulsion has formed, at a temperature substantially below the temperature of the first aliquot, and at a rapid rate so as to reduce the overall temperature of the composition preferably to below about 60° C. whereby the microemulsion or sub-micron emulsion structure is fixed.

A pharmaceutically active ingredient may suitably be incorporated in any one or more of the three parts of the formulation during preparation. The most appropriate part of incorporation will depend on the solubility characteristics of the pharmaceutically active ingredient and the preferred release profile of the resulting formulation. Preferably, a pharmaceutically active ingredient may be added in the third part with or without the non-surfactant amphiphilic type compound.

An occlusive agent which has the effect of adding emollient quality to the formulation is also desirably incorporated in the microemulsions or sub-micron emulsions by inclusion in the preparation of the first part of the composition. Preferably the occlusive agent is petrolatum.

The microemulsion or sub-micron emulsion resulting from the process is desirably gassed using a suitable propellant so as to be deliverable as a foam or mousse.

The present invention also provides an oil in water microemulsion or sub-micron emulsion composition for dermal delivery of at least one pharmaceutically active ingredient including an oil phase dispersed throughout a water phase, said oil phase including at least one selected from the group consisting of animal, mineral or vegetable oils, silanes, siloxanes, esters, fatty acids, fats, halogen compounds and alkoxylated alcohols; and at least one lipophilic surfactant, and said water phase including at least one hydrophilic surfactant, water and optionally non-surfactant amphiphilic compound, the weight ratio of said at least one hydrophilic surfactant to said at least one lipophilic surfactant being approximately 9.0:1.0 to 2.0:3.0.

Preferably, the present composition includes surfactants having an aggregated HLB number between 8.0 and 15.0, more preferably between 10 and 12 and still more preferably between 9.7 and 11.8. More preferably, the lipophilic surfactant has an HLB number of less than 10, and the hydrophilic surfactant has an HLB number of greater than 10.

The pharmaceutically active ingredient may suitably be in either or both said oil and/or water phases. The most appropriate phase of incorporation will depend on the solubility characteristics of the pharmaceutically active ingredient and the preferred release profile of the formulation.

An occlusive agent which has the effect of adding emollient quality to the formulation is also desirably present in the oil phase of the microemulsions or sub-micron emulsions. Preferably the occlusive agent is petrolatum.

The present invention also provides a method of medical or cosmetic treatment of a dermal condition including applying to the skin of a patient requiring such treatment an effective amount of oil in water microemulsion or sub-micron emulsion composition including at least one pharmaceutically active ingredient, including an oil phase dispersed throughout a water phase, said oil phase including at least one selected from the group consisting of animal, mineral or vegetable oils, silanes, siloxanes, esters, fatty acids, fats, halogen compounds and alkoxylated alcohols; and at least one lipophilic surfactant, and said water phase includes at least one hydrophilic surfactant, water and optionally a non-surfactant amphiphilic type compound, the weight ratio of the at least one hydrophilic surfactant to the at least one lipophilic surfactant being approximately 9.0:1.0 to 2.0:3.0.

DETAILED DESCRIPTION OF THE INVENTION

Figure 1:
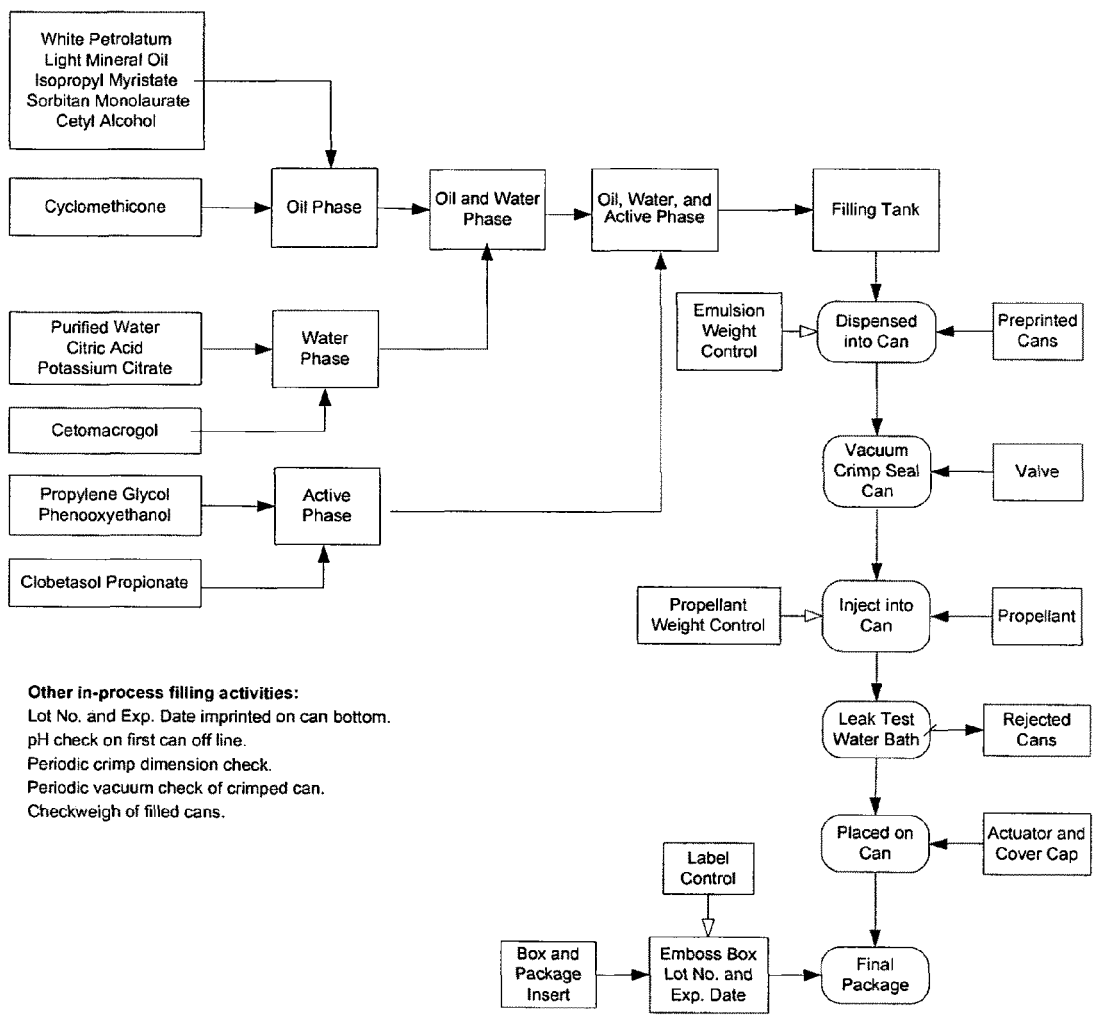
FIG. 1 is a schematic flow diagram showing one preferred embodiment of the invention in which an ethanol-free 0.05% clobetasol propionate microemulsion is prepared. The method is described in detail in Example 6.

Without being bound by theory, it is thought that when the non-surfactant, amphiphilic components such as propylene glycol, a typical polyol used in dermatological formulations because of its capacity as a penetration enhancer, and a solvent is present in the water phase, it interferes with the assembly or packing formation of the surfactants present in the composition around the oil particles and prevents the formation of microemulsion sized particles. The same is also true of a preservative, such as phenoxy ethanol or benzyl alcohol. By the process of the invention, it is possible to reproducibly manufacture microemulsion or sub-micron emulsion particles at low temperature in the range 100-600 nm with the majority of particles being in the 100-200 nm range. The exclusion of propylene glycol from the initial water/oil phase mixing appears to allow the surfactants present the ability to pack into a microemulsion structure at a lower temperature than would otherwise be achieved and with the assistance of temperature manipulation, to fix in place.

Throughout this specification, the term "non-surfactant, amphiphilic type compound" should be understood to include compounds which are miscible with water and other organic excipients, and which may act as a solvent for a pharmaceutically active ingredient not soluble in water, but may also have other functions in the formulations. Examples of compounds falling into the scope of this term are alcohols including propylene glycol, benzyl alcohol, dichlorobenzyl alcohol, phenoxyethanol, transcutol P, panthenol; polyols such as glycerin; alkoxylated alcohols including polyethylene glycol of varying molecular weight; heterocyclic compounds including methylpyrrolidine; and aprotic solvents including dimethyl sulfoxide. Preferred non-surfactant, amphiphilic type compounds are phenoxyethanol and propylene glycol. Phenoxyethanol may be present in amounts of up to 2% w/w and propylene glycol is desirably present in amounts of up to 50% w/w, more preferably in amounts of up to 30% w/w, and still more preferably in amounts of up to 25% w/w.

Throughout this specification the term "water soluble" when used in relation to a pharmaceutically active ingredient should be taken to mean compounds which have significant aqueous solubility and which typically exhibit low solubility in non-aqueous solvents.

The term "water insoluble" when used in relation to pharmaceutically active ingredients should be understood to include compounds which have no appreciable aqueous solubility and which typically favour hydrophobic solvents.

The term "phase assembly temperature" when used throughout this specification should be taken to mean the temperature at which maximum translucency of the dispersion is observed when preparing the oil in water microemulsions or sub-micron emulsions according to the processes described. This temperature point is consistent with the temperature at which tiny particles are assembled.

Preferably, in the present methods, processes and compositions according to the invention, the oil phase includes an occlusive agent which has the effect of adding an emollient quality to the formulations. One preferred occlusive agent is petrolatum. Although present at room temperature as a solid, using the process of preparation of the invention, it has been found that petrolatum can be successfully incorporated into a formulation which is of low viscosity and suitable for pressurised delivery. Other occlusive agents which may be incorporated in the compositions and according to the processes of the invention are microcrystalline wax, bees wax, paraffin wax and lanolin wax. Notably petrolatum, a preferred occlusive agent, is made up of approximately 50% w/w mineral oil and approximately 50% w/w microcrystalline and paraffin wax. Desirably the waxy component should not account for more than 25% w/w of the total oil phase.

Preferably in the present methods, processes and compositions of the invention the water phase of the formulation is added in two aliquots; in aliquots more preferably of about 70-80% and 20-30% by weight of the total water phase. More preferably still, the second aliquot is added after the microemulsion or sub-micron emulsion has formed, at a temperature substantially below the temperature of the first aliquot, and at a rapid rate so as to reduce the overall temperature of the composition preferably to below about 60° C. whereby the microemulsion or sub-micron emulsion structure is fixed. The two aliquots may both be an homogenous mix of all components in the phase or may be different components of the phase e.g. water together with non surfactant amphiphilic type compound and/or surfactant alone.

A pharmaceutically active ingredient may be introduced in any one or more of the three parts of preparation with the result that in the microemulsion or sub-micron emulsion according to the invention, the active ingredient may be present in the continuous water phase or the discontinuous oil phase or both. By appropriate manipulation, the formulations of the invention may be designed as slow or delayed release compositions by, for example, the location of the active ingredient in the phase in which it is substantially or completely insoluble.

Where the pharmaceutically active ingredient is introduced in the first part, optionally solvents, co-solvents and coupling agents may also be present. Preferred solvents may include acetyl tributylcitrate, tributyl citrate and other appropriate solvents. Coupling agents help link or improve miscibility of oils that are immiscible with the oil phase and assist in achieving clarity. Suitable coupling agents according to the invention are organic, non-ionic, virtually insoluble in water, miscible with oily/fatty/lipophilic materials and exhibit solubility for pasty and/or solid fatty/lipophilic materials. Isopropyl myristate is one suitable coupling agent. Others include, but are not limited to, polyglyceryl esters, isocetyl alcohol, octyl methoxycinnamate, octyl dimethyl PABA, tocopheryl acetate and lanolin alcohols.

Preferably the pharmaceutically active ingredient is introduced in the second part, and more preferably it is introduced in the third part where it appears that its presence alongside the non-surfactant, amphiphilic type compound serves to improve the transdermal performance of the composition. A non surfactant amphiphilic type compound also appears to assist in distributing the pharmaceutically active ingredient throughout the desired phase. In particular, where the pharmaceutically active ingredient is desirably present in both the oil phase and the water phase, non water miscible organic solvent is required in the oil phase and a water miscible organic solvent is required in the water phase. As the amount of water miscible organic solvent is increased, the rate of diffusion of the active agent across the skin barrier is seen to increase. A slower flux is observed when the active is dissolved within the oil phase that contains organic solvent. Particularly in the case that the pharmaceutically active ingredient is only sparingly soluble in water or insoluble in water, the addition of an increased amount of organic solvent to the water phase can assist in partitioning the pharmaceutically active ingredient into the water phase. Thus where the active agent is present in the continuous water phase, the active agent is available for rapid treatment of the patient's condition. Active agent in the oil phase may be available through other skin diffusion pathways for longer term treatment regimes.

The water phase may also include buffers such as, but not limited to, citric acid and potassium citrate, disodium EDTA and tetrasodium EDTA, disodium EDTA and disodium phosphate, and preservatives such as, but not limited to phenoxyethanol, benzyl alcohol, dichlorobenzyl alcohol, sorbic acid and potassium sorbate.

Where the pharmaceutically active ingredient is included in the water phase, this phase may also include a functional water soluble organic component including humectants, solvents for the active ingredient and penetration enhancers. Substances which may be included in the formulations of the invention in the water phase and which fall into one or more of these categories include but are not limited to propylene carbonate, transcutol, ethoxydiglycol, polyhydric alcohols such as glycerol, sorbitol and propylene glycol.

The pharmaceutically active ingredient may be any chemical substance or combination of chemical substances which have registration for the purposes of cosmetic or medical treatment and which are dermally deliverable. The pharmaceutically active ingredients can be present in the composition in different forms, depending on which form yields the optimum delivery characteristics. Thus, in the case of drugs, it can be in its free base or acid form, or in the form of salts, esters, or any other pharmacologically acceptable derivatives, or as components of molecular complexes, analogues, metabolites or pro-drugs.

In one preferred embodiment of the invention, the pharmaceutically active ingredient can be a compound which is insoluble or sparingly soluble in the water. In another preferred embodiment of the invention, the pharmaceutically active ingredient can be a water soluble compound.

Preferably the active ingredient is a corticosteroid selected from the group consisting of betamethasone valerate, desonide and clobetasol propionate or vitamin D or vitamin A analogues. The pharmaceutically active ingredient may alternatively be a drug that is normally delivered by oral, parenteral, percutaneous, perungual or rectal route.

Other examples of pharmaceutically active ingredients that can be administered by the compositions of this invention include, but are not limited to:

Cardioactive medications, for example, organic nitrates such as nitroglycerine, isosorbide dinitrate, and isosorbide mononitrates; quinidine sulfate; procainamide; thiazides such as bendroflumethiazide, chlorothiazide, and hydrochlorothyazide; nifedipine; nicardipine; adrenergic blocking agents, such as timolol and propranolol; verapamil; diltiazem; captopril; clonidine and prazosin.

Androgenic steroids, such as testosterone, methyltestosterone and fluoxymesterone.

Estrogens, such as conjugated estrogens, esterified estrogens, estropipate, 17beta estradiol, 17beta-estradiol valerate, equilin, mestranol, estrone, estriol, 17beta-ethinyl estradiol, and diethylstilboestrol. Progestational agents, such as progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17alpha hydroxyprogesterone, dydrogesterone, dimethisterone, ethinylestrenol, norgestrel, demegestone, promegestone, and megestrol acetate.

Drugs having an action on the central nervous system, for example sedatives, hypnotics, antianxiety agents, analgesics and anaesthetics, such as chloral, buprenorphine, naloxone, haloperidol, fluphenazine, pentobarbital, phenobarbital, secobarbital, codeine, lidocaine, tetracaine, dyclonine, dibucaine, methocaine, cocaine, procaine, mepivacaine, bupivacaine, etidocaine, prilocalne, benzocaine, fentanyl, and nicotine.

Nutritional agents, such as vitamins, essential amino adds and essential fats.

Anti-inflammatory agents, such as hydrocortisone, cortisone, dexamethasone, fluocinolone, triamcinolone, medrysone, prednisolone, flurandrenolide, prednisone, halcinonide, methylprednisolone, flurandrenolide, prednisone, halcinonide, methylprednisolone, fludrocortisone, corticosterone, paramethasone, betamethasone, ibuprofen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like.

Respiratory agents, such as theophylline and beta2-adrenergic agonists such as albuterol, terbutaline, metaproterenol, ritodrine, carbuterol, fenoterol, quinterenol, rimiterol, solmefamol, soterenol, and tetroquinol.

Sympathomimetics, such as dopamine, norepinephrine, phenylpropanolamine, phenylephrine, pseudoephedrine, amphetamine, propylhexedrine and epinephrine. Miotics, such as pilocarpine, and the like. 12 Cholinergic agonists, such as choline, acetylcholine, methacholine, carbachol, bethanechol, pilocarpine, muscarine, and arecoline.

Antimuscarinic or muscarinic cholinergic blocking agents such as atropine, scopolamine, homatropine, methscopolamine, homatropine methylbromide, methantheline, cyclopentolate, tropicamide, propantheline, anisotropine, dicyclomine, and eucatropine. Mydriatics, such as atropine, cyclopentolate, homatropine, scopolamine, tropicamide, eucatropine and hydroxyamphetamine.

Psychic energizers such as 3-(2-aminopropyl)indole, 3-(2-aminobutyl)indole, and the like.

Anti-infectives, such as antivirals, e.g. acyclovir, allylamines and in particular terbinafine hydrochloride and naftifine hydrochloride antibiotics, including penicillin, tetracycline, chloramphenicol, sulfacetamide, sulfamethazine, sulfadiazine, sulfamerazine, sulfamethizole and sulfisoxazole; antivirals, including idoxuridine; antibacterials, such as erythromycin and clarithromycin; and other anti-infectives including nitrofurazone and the like.

Vitamins such as vitamins A, D and E, and derivatives thereof, such as retinal, tretinoin, isotretinoin, retinol, retinoxytrimethylsilane, retinyl acetate, retinyl linoleate, retinyl palmitate, retinyl propionate and other vitamin A analogues for vitamin A derivatives, alfacalcidol, calcitriol, tacalcitol, calcipotriol, calcifediol, colecalciferol, dihydrotachysterol, ergocalciferol, doxercalciferol, falecalcitriol, maxacalcitol, paracalcitol and other vitamin D analogues for vitamin D derivatives, and tocopherols, tocophersolan, tocopheryl acetate, tocopheryl glucoside, tocopheryl linoleate, tocopheryl nicotinate, tocopheryl oleate, tocopheryl succinate and other vitamin E analogues for vitamin E derivatives.

Hydroxyacids useful for various conditions and disorders including age spots, keratoses, skin wrinkles etc., such as 2-Hydroxyacetic acid; 2-hydroxypropanoic acid (=lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihyroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxphenyl)lactic acid; 3-(4-hydroxyphenyl)lactic acid; hexahydromandelic acid; 3-hydroxy-3-methylpentanoic acid; 4-hydroxydecanoic acid; 5-hydroxydecanoic acid; aleuritic acid. 2-Hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutanedioic acid; or its salts;

Citric acid, isocitric acid, agaricic acid, quinic acid, glucuronic acid, glucuronolactone, galacturonic acid, galacturonolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid, or its salts; and Pyruvic acid, hydroxypyruvic acid, hydroxypyruvic acid phosphate, their esters; methyl pyruvate, ethyl pyruvate, propyl pyruvate, isopropyl pyruvate; phenyl pyruvic acid, its esters; methyl phenyl pyruvate, ethyl phenyl pyruvate, propyl phenyl pyruvate; formyl formic acid; its esters; methyl formyl formate, ethyl formyl formate, propyl formyl formate; benzoyl formic acid, its esters; methyl benzoyl formate, ethyl benzoyl formate and propyl benzoyl formate; 4-hydroxybenzoyl formic acid, its esters; 4-hydroxyphenyl pyruvic acid, its esters; 2-hydroxyphenyl pyruvic acid and its esters. Lactic acid, salts thereof and mixtures thereof are preferred.

Anti-itch compounds such as local anesthetics, antihistamines, corticosteroids and anti-pruritics.

Local anesthetics including but not limited to articaine, bupivacaine, cinchocaine, ethyl parapiperidinoacetylaminobenzoate, etidocaine, levobupivacaine, lidocaine, mepivacaine, oxetacaine, prilocalne, ropivacaine, tolycaine, trimecaine, amylocalne, cocaine, propanocaine, proxymetacaine, benzocaine, butacaine, butoxycaine, butyl aminobenzoate, chloroprocaine, oxybuprocaine, parethoxycaine, procaine, propoxycaine, tetracaine, tricaine, diperodon, dyclonine, ethyl chloride, ketocaine, myrtecaine, octacaine, pramocaine (=pramoxine), propipocaine, quinisocaine, and the like, including salts thereof and mixtures thereof, with pramoxine and pramoxine HCl being preferred.

Antihistamines including but not limited to diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, and chlorpheniramine.

Antipruritics including but not limited to calamine, camphor, methol, Palmitamide MEA, stearamide MEA, lactamide MEA, oleamide MEA, acetamide MEA, and mixtures thereof, some of these also having anti-inflammatory effects.

Humoral agents, such as the prostaglandins, natural and synthetic, for example PGE1, PGF2alpha, and PGF2alpha, and the PGE1 analog misoprostol.

Antispasmodics, such as atropine, methantheline, papaverine, cinnamedrine, and methscopolamine.

Antidepressant drugs, such as isocarboxazid, phenelzine, tranylcypromine, imipramine, amitriptyline, trimipramine, doxepin, desipramine, nortriptyline, protriptyline, amoxapine, maprotiline, and trazodone.

Anti-diabetics, such as insulin, and anticancer drugs such as tamoxifen and methotrexate.

Anorectic drugs, such as dextroamphetamine, methamphetamine, phenylpropanolamine, fenfluramine, diethylpropion, mazindol, and phentermine. Anti-allergenics, such as antazoline, methapyrilene, chlorpheniramine, pyrilamine and pheniramine.

Tranquilizers, such as reserpine, chlorpromazine, and anti-anxiety benzodiazepines such as alprazolam, chlordiazepoxide, clorazeptate, halazepam, oxazepam, prazepam, clonazepam, flurazepam, triazolam, lorazepam and diazepam.

Antipsychotics, such as thiopropazate, chlorpromazine, triflupromazine, mesoridazine, piperacetazine, thioridazine, acetophenazine, fluphenazine, perphenazine, trifluoperazine, chlorprathixene, thiothixene, haloperidol, bromperidol, loxapine, and molindone.

Decongestants, such as phenylephrine, ephedrine, naphazoline, Antipyretics, such as aspirin, salicylamide, and the like.

Antimigraine agents, such as dihydroergotamine and pizotyline.

Drugs for treating nausea and vomiting, such as chlorpromazine, perphenazine, prochlorperazine, promethazine, scopolamine, hyacine hydrobromide, triethylperazine, triflupromazine, and trimeprazine.

Anti-malarials, such as the 4-aminoquinolines, alpha-aminoquinolines, chloroquine, and pyrimethamine.

Anti-ulcerative agents, such as misoprostol, omeprazole, and enprostil.

Peptides and proteins, such as drugs for Parkinson's disease, spasticity, and acute muscle spasms, such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, insulin, erythropoietin and growth hormone.

Anti-estrogen or hormone agents, such as tamoxifen or human chorionic gonadotropin.

Nucleotides and nucleic acids (e.g. DNA).

The third part may be present in the compositions according to the invention in an amount from 0.1% w/w to 50% w/w.

The first part of the methods, processes and compositions according to the invention preferably makes up 1-30% w/w of the total resulting composition. Individual components of this phase preferably each have a solubility parameter of approximately 5.7-8.1 cal/cc and together, more preferably, when combined, have a calculated solubility parameter of approximately 7.0-7.4 cal/cc and should still more preferably be in a liquid state at the phase assembly temperature of the composition.

Oils that may be used in the methods, processes and compositions according to the invention may include but are not limited to one or more of mineral oils, petrolatum, caprylic/capric triglyceride, peanut oil, cyclomethicone, cod liver oil, isopropyl myristate and alkoxylated oils including ethoxylated, propoxylated or ethoxylated-propoxylated oils. Cosmetic grade oils such as dioctyl cyclohexane, cetearyl isononanoate, C12-C15 alkyl benzoate, oleyl oleate, octylhydroxy stearate and octyl dodecanol may also be suitable. In preferred processes, methods and compositions according to the invention, the oil phase includes petrolatum, mineral oil, esters and cyclomethicone. Still more preferably, the oil phase includes petrolatum, mineral oil, an ester being isopropyl myristate, acetyl tributylcitrate, or tributylcitrate and cyclomethicone in an approximate ratio of 1:1:1:1. Still more preferably the oil phase includes approximately 25% petrolatum, 25% mineral oil, 25% isopropyl myristate and 25% cyclomethicone. One of the problems confronted with conventional emulsion formulations is the extent to which they have to be redispersed if, on standing, a separation occurs. The ability to redisperse is important to the commercial acceptability of a product. In the methods, processes and compositions according to the invention, this issue has been addressed by optimising the oil phase to reduce the proportion of petrolatum, introduce co solvents and coupling agents and reduce the presence of any solid surfactants that exhibit solubility in the oil phase whilst ensuring the surfactant remains functional.

Other components of the oil phase might include but are not limited to lauryl lactate, isosteareth-2-octanoate, alk-oxylated derivates of lauric, oleic or stearic acid, each of which may act as emulsifiers, humectants, or coupling agents; octyl salicylate and oleyl oleate which may act as skin penetrants; polyglyceryl-3-laurate, diisopropyl sebacate which may act as an emollient, solubiliser or coupling agent or Hydramol PGPL (PEG.PPG-8/3 laurate).

The total amount of oil in the oil phase may be in the amount of about 1-30% w/w.

The nature of surfactants (also known as emulsifiers) which can be utilised in the compositions resulting from the preferred processes of the invention will vary, and as discussed in the preamble of this specification may be subject to some experimentation before being perfected. Variations may arise as a result of the components of the oil phase selected, the pharmaceutically active ingredient and possibly even the temperature parameters under which the process is conducted.

Generally, commercial microemulsion gels are based on phosphate esters and non-ionic emulsifers, although it is possible to formulate systems based on non-ionic emulsifiers alone. Ethoxylated fatty alcohols are the most popular non-ionic emulsifiers used. These include ethoxylates of: lanolin alcohols (laneths) oleyl alcohol (oleths), lauryl alcohol (laureths), cetyl alcohols (ceteths), stearyl alcohol (steareths), cetostearyl alcohols (ceteareths) and isocetyl alcohol (isoceteths). Phosphate esters include those based on ethoxylated lauryl alcohol (laureth phosphates) and ethoxylated oleyl alcohol (oleth phosphates). In general, the more ethoxylated a surfactant is, the higher its HLB, the higher the temperature at which a microemulsion or sub-micron emulsion is formed, and the larger the particle size of the resulting formulation. Ethoxylation has a greater effect on the ability of the composition to assemble as a microemulsion or sub-micron emulsion than does the carbon chain length of the surfactant.

When discussing emulsifiers for microemulsion gels, it is helpful to keep in mind that a large molecular weight emulsifier and a small molecular weight oil may be the optimum combination.

In the processes, methods and compositions according to one preferred embodiment of the invention, lipophilic non-ionic surfactants may be selected from the group consisting of fatty alcohols such as cetyl alcohol, isocetyl alcohol or stearyl alcohol; glyceryl esters and derivatives thereof such as glyceryl monostearate and glyceryl monooleate; esters such as methyl glucose sesquistearate; sorbitan derivatives such as sorbitan laurate, sorbitan monopalmitate, sorbitan monostearate, sorbitan monooleate and sorbitan sesquioleate. Lipophilic anionic surfactants may be selected from the group consisting of fatty acids such as palmitic acid and stearic acid. Hydrophilic non-ionic surfactants may be selected from the group consisting of alkoxylated carboxylic acids such as PEG 40 stearate; alkoxylated alcohols such as ceteareth −12, −20 and −30, oleth 10 and laureth −4 and −23 and steareth-4; sorbitan derivatives such as polysorbate 40, polysorbate 60 and polysorbate 80; glyceryl esters and derivatives thereof such as PEG-40 hydrogenated castor oil and PEG-35 castor oil.

The minimum concentration of surfactant in the methods, processes and compositions according to one form of the invention appears to be about 1.8% w/w using 1% w/w oil phase. The maximum concentration of surfactant in the compositions according to one form of the invention appears to be about 20.1% w/w using 10% w/w oil phase.

It also appears that the ratio of surfactant:oil may also contribute to the ability of the compositions prepared according to the processes of the invention to form sub-micron emulsions and microemulsions. A preferred ratio of surfactant:oil is approximately 1:3 to 3:1

In the compositions of the invention, the surfactant system includes at least two surfactants, one lipophilic and one hydrophilic. Preferably, the surfactant system includes surfactants having an aggregated HLB number between 8.0 and 15.0, more preferably between 10 and 12 and still more preferably between 9.7 and 11.8. More preferably, the lipophilic surfactants have an HLB number of less than 10, and the hydrophilic surfactants have an HLB number of greater than 10. Preferred candidates as surfactants in the compositions according to the invention are sorbitan laurate and cetyl alcohol used in the first oil phase, and Ceteareth-20 or oleth 10 in the second water phase.

In a two surfactant system (one lipophilic and one hydrophilic), the preferred range of concentration of hydrophilic:lipophilic surfactant is about 9:1 to 1.0:1.0.

In a three surfactant system using one hydrophilic surfactant and two lipophilic surfactants, one preferred ratio of surfactants is 8:1:1 to 4:5:1. That is the total hydrophilic:lipophilic ratio is preferably 4:1 to 2:3.

In a four surfactant system using two hydrophilic surfactants and two lipophilic surfactants, one preferred ratio of surfactants is 2.5:2.5:4.0:1.0 to 3.0:3.0:3.0:1.0. That is the total hydrophilic:lipophilic ratio is preferably 3.0:2.0 to 1:1.

Other additives which may be present in the compositions prepared according to the invention not already mentioned include but are not limited to preservatives such as phenoxyethanol, benzyl alcohol, dichlorobenzyl alcohol, sorbic acid and potassium sorbate; antioxidants such as BHT, humectants such as lactic acid, glycerine, urea and Ajidew N-50/Sodium PCA; and polymers, thickeners or gums such as Eudragit NE40D. These additives are typically organic and exhibit some miscibility with water and other organic ingredients and may generally be incorporated together with the active agent.

The compositions according to the invention may be in any physical form so as to suit their purpose. In a final fourth part, or a final fifth part when a fourth part comprising a preservative is present, of the process of preparation of the microemulsions or sub-micron emulsions of the invention it is possible to introduce a propellant into the microemulsion so that the composition may be dispensed as an aerosol foam or mousse. In this case the propellant may be selected from hydrocarbons such as P70; ethers such as dimethylether and halogen compounds such as Hydrofluorocarbon 134A. The propellant may be present in amounts of about 5-20% w/w.

The microemulsion or sub-micron emulsion may also be formulated as a gel, cream, lotion or patch depending on its purpose. For example, thickening agents such as sodium carboxymethyl cellulose or gelling agents such as the water soluble polymers, carbomer and xanthan may be added when a gel formulation is required.

The following examples provide more details of the microemulsion or sub-micron emulsion formulations of the invention, preparation methods and storage stability thereof; however, the following examples are provided only to illustrate the scope of the invention but should not be considered to limit the scope to the examples as the skilled person will appreciate the means by which the following formulations may be altered whilst still resulting in formulations falling within the broadest scope of the invention.

EXAMPLES

Examples 1 and 1A show a composition having surfactant ratios according to the prior art, and wherein propylene glycol, generally considered disruptive of sub-micron emulsions is added together with other constituents in a single stage aqueous phase of the process. These examples are provided for comparison purposes and do not illustrate the invention.

Examples 2-5A show six different compositions using the pharmaceutically active ingredients clobetasol propionate, desonide or betamethasone-17-valerate in formulations according to preferred embodiments of the invention wherein the surfactant ratios are of the desired ratio range. Examples 4 and 5 in accordance with the invention are compositions which include propellant. The examples 2-5A may be further processed into formulations useful as a lotion, spray, gel, paste, foam or any other suitable dosage form.

Example 1

Prior Art

|  | 20% PG/pH 6 % w/w |
| --- | --- |
| Phase 1 - Oil Phase |  |
| Clobetasol Propionate | 0.0475 |
| Petrolatum | 7.50 |
| Mineral Oil | 5.00 |
| Isopropyl Myristate | 7.50 |
| Cyclomethicone | 5.00 |
| Cetyl Alcohol | 2.00 |
| Sorbitan Laurate | 1.50 |
| Phase 2 - Aqueous Phase |  |
| Water | 38.7525 |
| Ceteareth-20 | 6.50 |
| Citric Acid | 0.04 |
| Potassium Citrate | 0.16 |
| Propylene Glycol | 20.00 |
| Phenoxy Ethanol | 1.00 |

|  | 20% PG/pH 6 % w/w |
| --- | --- |
| Phase 3 - Propellant Phase |  |
| Hydrocarbon Propellant P70 | 5.00 |
| Total | 100.00 |

Example 1A

Prior Art

|  | 20% PG/pH 6 % w/w |
| --- | --- |
| Phase 1 - Oil Phase |  |
| Clobetasol Propionate | 0.05 |
| Petrolatum | 7.90 |
| Mineral Oil | 5.26 |
| Isopropyl Myristate | 7.90 |
| Cyclomethicone | 5.26 |
| Cetyl Alcohol | 2.11 |
| Sorbitan Laurate | 1.58 |
| Phase 2 - Aqueous Phase |  |
| Water | 40.79 |
| Ceteareth-20 | 6.84 |
| Citric Acid | 0.04 |
| Potassium Citrate | 0.17 |
| Propylene Glycol | 21.05 |
| Phenoxy Ethanol | 1.05 |
| Emulsion concentrate Total | 100.00 |

Examples 1 and 1A show a surfactant ratio of Ceteareth-20:sorbitan laurate:cetyl alcohol of 6.5:1.5:2.0 wherein propylene glycol is introduced in one stage to the aqueous phase of the composition. This product separates on standby, has poor in-can redispersability and requires continuous mixing in process which is costly in large scale manufacture.

Example 2

|  | 20% PG/pH 5 % w/w |
| --- | --- |
| Part 1 |  |
| Petrolatum | 7.90 |
| Mineral Oil | 5.26 |
| Isopropyl Myristate | 7.90 |
| Cyclomethicone | 5.26 |
| Cetyl Alcohol | 1.05 |
| Sorbitan Laurate | 4.74 |
| Part 2 |  |
| Water | 40.79 |
| Ceteareth-20 | 4.74 |
| Citric Acid | 0.04 |
| Potassium Citrate | 0.17 |

-continued

|  | 20% PG/pH 5 % w/w |
|---|---|
| Part 3 | |
| Propylene Glycol | 21.05 |
| Phenoxy Ethanol | 1.05 |
| Clobetasol Propionate | 0.05 |
| Emulsion concentrate Total | 100.00 |

Example 2 shows a surfactant ratio of Ceteareth-20:sorbitan laurate cetyl alcohol of 4.5:4.5:1.0.

Example 3

|  | 17% PG/pH 5 % w/w |
|---|---|
| Part 1 | |
| Petrolatum | 5.26 |
| Mineral Oil | 5.26 |
| Isopropyl Myristate | 10.53 |
| Cyclomethicone | 2.63 |
| Cetyl Alcohol | 1.05 |
| Sorbitan Laurate | 4.74 |
| Part 2 | |
| Water | 46.58 |
| Ceteareth-20 | 4.74 |
| Citric Acid | 0.08 |
| Potassium Citrate | 0.13 |
| Part 3 | |
| Propylene Glycol | 17.90 |
| Phenoxy Ethanol | 1.05 |
| Desonide | 0.05 |
| Emulsion concentrate Total | 100.00 |

Examples 3 shows a surfactant ratio of Ceteareth-20:sorbitan laurate:cetyl alcohol of 4.5:4.5:1.0.

Example 4

|  | 5% PG % w/w |
|---|---|
| Part 1 | |
| Petrolatum | 5.00 |
| Mineral Oil | 5.00 |
| Isopropyl Myristate | 5.00 |
| Cyclomethicone | 5.00 |
| Cetyl Alcohol | 1.00 |
| Sorbitan Laurate | 4.00 |
| Part 2 | |
| Water | 58.686 |
| Ceteareth-20 | 5.00 |
| Citric Acid | 0.20 |
| Potassium Citrate | |

-continued

|  | 5% PG % w/w |
|---|---|
| Part 3 | |
| Propylene Glycol | 5.00 |
| Phenoxy Ethanol | 1.00 |
| Betamethasone-17-Valerate | 0.114 |
| Part 4 | |
| Hydrocarbon Propellant P70 | 5.00 |
| Total | 100.00 |

Example 4A

|  | 5% PG % w/w |
|---|---|
| Part 1 | |
| Petrolatum | 5.26 |
| Mineral Oil | 5.26 |
| Isopropyl Myristate | 5.26 |
| Cyclomethicone | 5.26 |
| Cetyl Alcohol | 1.05 |
| Sorbitan Laurate | 4.21 |
| Part 2 | |
| Water | 61.80 |
| Ceteareth-20 | 5.26 |
| Citric Acid | 0.21 |
| Potassium Citrate | |
| Part 3 | |
| Propylene Glycol | 5.26 |
| Phenoxy Ethanol | 1.05 |
| Betamethasone-17-Valerate | 0.12 |
| Emulsion concentrate Total | 100.00 |

Examples 4 and 4A show a surfactant ratio of Ceteareth-20:sorbitan laurate:cetyl alcohol of 5.0:4.0:1.0.

Example 5

|  | 10% PG % w/w |
|---|---|
| Part 1 | |
| Petrolatum | 5.00 |
| Mineral Oil | 5.00 |
| Isopropyl Myristate | 5.00 |
| Cyclomethicone | 5.00 |
| Cetyl Alcohol | 1.00 |
| Sorbitan Laurate | 4.00 |
| Part 2 | |
| Water | 53.686 |
| Ceteareth-20 | 5.00 |
| Citric Acid | 0.20 |
| Potassium Citrate | |
| Part 3 | |
| Propylene Glycol | 10.00 |
| Phenoxy Ethanol | 1.00 |
| Betamethasone-17-Valerate | 0.114 |

-continued

| | 10% PG<br>% w/w |
|---|---|
| Part 4 | |
| Hydrocarbon Propellant P70 | 5.00 |
| Total | 100.00 |

Example 5A

| | 10% PG<br>% w/w |
|---|---|
| Part 1 | |
| Petrolatum | 5.26 |
| Mineral Oil | 5.26 |
| Isopropyl Myristate | 5.26 |
| Cyclomethicone | 5.26 |
| Cetyl Alcohol | 1.05 |
| Sorbitan Laurate | 4.21 |
| Part 2 | |
| Water | 56.53 |
| Ceteareth-20 | 5.26 |
| Citric Acid | 0.21 |
| Potassium Citrate | |
| Part 3 | |
| Propylene Glycol | 10.53 |
| Phenoxy Ethanol | 1.05 |
| Betamethasone-17-Valerate | 0.12 |
| Emulsion Concentrate Total | 100.00 |

Examples 5 and 5A show a surfactant ratio of Ceteareth-20:sorbitan laurate:cetyl alcohol of 5.0:4.0:1.0.

The examples 2-5A show good physical stability, utilise less expensive manufacturing techniques and show good redispersability.

Example 6

FIG. 1 shows the preparation of an ethanol-free 0.05% clobetasol propionate foam of the same type as example 2 according to one preferred process according to the invention. This process has been successfully scaled up as follows.

Petrolatum, light mineral oil, isopropyl myristate, sorbitan monolaurate and cetyl alcohol are added in specified quantities to the primary compounding tank as the oil phase. This phase is mixed in the tank and heated to 75-80° C. Cyclomethicone is added and mixing is continued at 75-80° C. until the oil phase is uniform in consistency.

To make the water phase, purified water, citric acid and potassium citrate are added into a kettle. This water phase mixture is mixed and heated to 80-85° C. Ceteareth-20 is then added and mixing is continued at 80-85° C. until complete dissolution of all components occurs.

The third part containing the active agent ("the active phase") is prepared by adding specified quantities of propylene glycol and phenoxyethanol into a kettle. Mixing of this part is commenced, the active agent, clobetasol propionate is added and the phase is heated to 55-60° C. Mixing is continued until complete dissolution of all components occurs. The temperature of this part is allowed to cool, or is cooled in a water bath to 30° C.

Approximately 70% of the water phase mixture is then added to the oil phase mixture in the primary compounding tank. The two phases are mixed together and heated to 85-90° C. The approximately 30% remaining of the water phase is cooled to 20-25° C. in a chilled water bath. After continued mixing of the oil/water phase in the primary compounding tank and cooling of the mixture to 72-78° C., the remainder of the water phase mixture (approximately 30%) is added to the oil/water phase in the primary compounding tank. Simultaneously, cooling is commenced to achieve a temperature of 35-40° C.

The content of the active phase kettle is added to the oil/water phase mixture in the primary compounding tank. Mixing is continued and the temperature is lowered to 20-25° C.

The resultant composition is dispensed into cans at ambient temperature.

Example 7

This example details the preparation of a Desonide formulation according to one preferred process of the invention. The method results in a 17% Propylene Glycol and Desonide composition. This process has not been scaled up.

The item numbers in the following composition listing correspond to the item numbers in the process description which follows.

| Item No. | Ingredient | % w/w | % w/w without Propellant |
|---|---|---|---|
| | Part 1 | | |
| 1 | Snow White Petrolatum | 5.00 | 5.263 |
| 2 | Lt Mineral Oil (Drakeol 5) | 5.00 | 5.263 |
| 3 | Isopropyl Myristate | 10.00 | 10.526 |
| 4 | ST-Cyclomethicone 5-NF | 2.50 | 2.632 |
| 5 | Cetyl Alcohol | 1.00 | 1.053 |
| 6 | Sorbitan Laurate (Crill 1) | 4.50 | 4.737 |
| | Part 2<br>(Part 2A = 70%, Part 2B = 30%) | | |
| 7 | Purified water | 44.2525 | 46.582 |
| 8 | Ceteareth-20 | 4.50 | 4.737 |
| 9 | Citric Acid, anhydrous | 0.076 | 0.080 |
| 10 | Potassium Citrate, monohydrate | 0.124 | 0.131 |
| | Part 3 | | |
| 11 | Propylene Glycol | 17.00 | 17.895 |
| 12 | Phenoxyethanol | 1.00 | 1.053 |
| 13 | Desonide | 0.0475 | 0.050 |
| | Part 4 | | |
| 14 | Propellant P70 | 5 | |
| | TOTAL | 100.00 | 100.00 |

Items 1 to 6 are added to the mixing vessel, stirred and heated to 60-80° C. to form the oil phase. The temperature is maintained or re-established before adding the water phase (see below).

To prepare the water phase, water at room temperature, anhydrous citric acid and potassium citrate, monohydrate are added to a suitably sized vessel and stirred together. Ceteareth-20 is added, and the mixture is heated to a maximum of 50° C. until the ceteareth-20 is completely dissolved.

The water phase is separated into two parts. About 30% of the water phase mixture is cooled to 20-30° C. The remaining 70% of the water phase mixture is added to the oil phase mixing vessel at its existent temperature. The mixing vessel containing the oil phase and most of the water phase is heated to 80-85° C. with thorough mixing to ensure uniformity. The temperature should be held at this level for about 10 minutes to assist in obtaining uniformity. The mixture will be a water in oil emulsion and will be very white in colour. The conductivity will be less than 100 µs/cm.

The oil in water mixture should be allowed to cool to about 73° C. When approaching the assembly temperature the rate of cooling should be no more than 1° per minute. At the assembly temperature the Δconductivity changes from a large negative value to an almost constant value.

When the mixing vessel reaches about 73° C. as described, the remaining 30% of the water phase which is at 20-30° C. is added and the mixing vessel is immediately cooled. Rapid addition of the remaining quantity of water phase is desirable, and the temperature of the mixture should be approximately 60° C. at the completion of the addition of the remaining water phase mixture.

Phase 3 containing propylene glycol is prepared by adding items 11 to 13 to a suitable vessel and heating until the Desonide is dissolved. After dissolution of the Desonide, the mixture should be cooled to less than 30° C. The oil in water emulsion mixture should be cooled to about 35-40° C. by stirring and phase 3 is then added at a rate so that the entire mixture is not added until at least 5-10 minutes has elapsed. An unsatisfactory addition rate will be evidenced by the presence of a bilayered product having an oily film on top upon standing.

The mixing vessel containing all components is cooled by stirring to about 25-30° C. The resultant emulsion should be maintained at about 20-25° C. before filling and should remain homogenous for at least 48 hours without stirring.

Temperatures may vary up to about 5° C. depending on the sorbitan laurate (oil phase) used. Conductivity tests are recommended to determine the set point or assembly temperature of the microemulsion.

Example 8

This example demonstrates the effect on the compositions of varying the parameters of surfactant ratio, pre set point temperature variation and post set point cooling rate.

Figure 2:
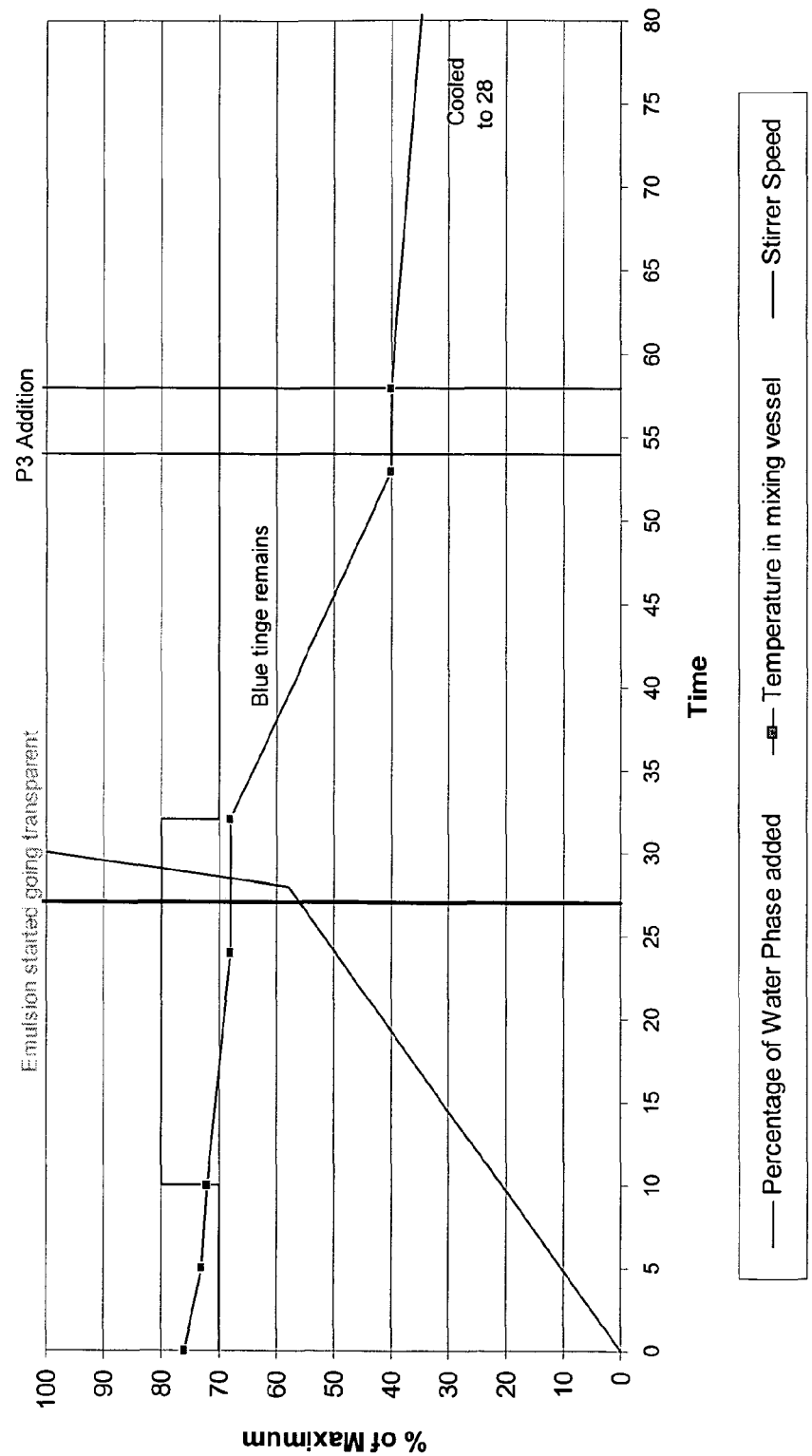
FIG. 2 is a graphical representation of one preferred method of preparation of formulations according to the invention utilising the corticosteroid clobetasol propionate.

Table 1 summarises the effects of varying the parameters of the preparation of mainly 1.5 kg batches of compositions according to preferred aspects of the invention. As is shown in the table, the ratio of Ceteareth-20:sorbitan laurate is adjusted, the temperature of the phase 1 and phase 2 mixes prior to combination, and subsequent to combination, is adjusted and the cooling rate of the combination of the two phases is adjusted and observations of the appearance, stability and particle size are made. Batch numbers 367-14, 367-16, 367-22, E207/111 and 328-68 were considered successful. FIG. 2 is a graphical representation of the method of this example charting the rate of addition of the various components of the compositions.

TABLE 1

Summary of Scale-up Process Development E foams in 1.5 kg Batches:
Desonide P1 = 442 g P2 = 773 g P3 = 285 g Clobetasol propionate P1 = 482 g P2 = 686 g P3 = 332 g

| Batch No | Ceteareth-20 to Sorbitan laurate | Temp P1-P2 | P2 addition | Cooling Rate to 40° C. | Observations during P2 addition | Size (Microscope) | Emulsion appearance | Stability at R.T. |
|---|---|---|---|---|---|---|---|---|
| Desonide E | | | | | | | | |
| 367-12 | 5.0:4.0 | 82° C.-82° C. Maintained | 100 ml pipette | Quickly to 40° C. with tap water, 5-10 min | Went translucent then white before P2 completely added | Many 1-2 µm | White, leaves white residue on glass | <12 hr |
| 367-14 | 4.5:4.5 | 82° C.-82° C. Maintained | 50 ml pipette | Quickly to 40° C. with tap water, 5-10 min | Went translucent later than for 367-12, stayed longer before going white before P2 completely added | ≦1 µm | White but less residue on glass than 367-12 | >5 days |
| 367-16 | 4.5:4.5 | 75° C.-75° C. (65° C.) | Pump - 130 ml min$^{-1}$ | 35 min to cool to 40° C. | Same as 367-14 | <1 µm | White, but quite clear on glass | >5 days |
| 367-18 | 4.0:5.0 | 75° C.-75° C. (65° C.) | Pump - 130 ml min$^{-1}$ | 35 min to cool to 40° C. | Went translucent later than for 367-14, went white just after P2 added | ≦1 µm | | <1 day, just see |
| 367-22 | 4.5:4.5 | 72° C.-80° C. (68° C.) | Pump - 112 ml min$^{-1}$ for 6 m 6 s High speed for remainder, <1 min | Cooling begun immediately - 25 min to 40° C. | Went translucent at 6 min, then remained quite translucent after P2 added. | <<1 µm | Blue-White V clean on glass, looks very transparent | >5 days |
| Clobetasol propionate | | | | | | | | |
| E207/1/1 500 ml | 4.5:4.5 | 75° C.-75° C. not maintained | Hand poured | Air cooled in about 45 min | Stayed quite translucent. | <<1 µm | Blue-White V clean on glass, looks very transparent | >5 days |
| 328-68 | 4.5:4.5 | 72° C.-80° C. (68° C.) | Pump - 112 ml min$^{-1}$ for 5 min High speed for remainder (2 min) | Cooling begun immediately - 25 min to 40° C. | Went translucent at 5 min, then remained quite translucent after P2 added. | <<1 µm just see dots | Blue-White V clean on glass, looks transparent | >5 days |

KEY:
P1 - Phase 2 (oil)
P2 - Phase 2 (aqueous)
P2 addition: 100 ml pipette - Constant, stop start using a 100 ml pipette
Pump - constant addition using a peristaltic pump. P2 would cool in the tubing giving resulting in the temperature shown in brackets.

Example 9

Figure 3:
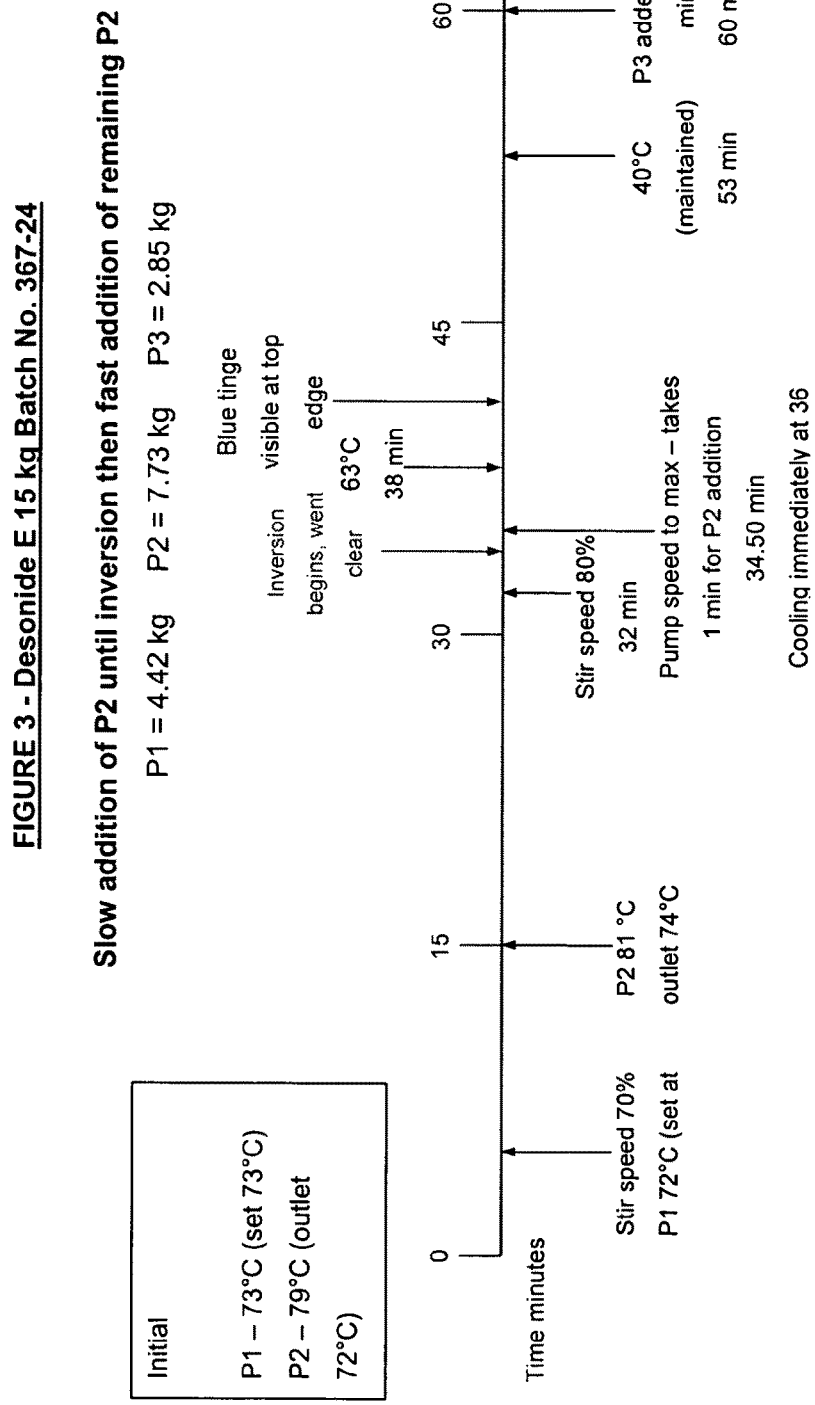
FIG. 3 is a timeline of one preferred method of preparation of formulations according to the invention utilising the corticosteroid desonide.

FIG. 3 shows the timeline of a preferred process of preparation of a large scale 15 kg Desonide composition according to one aspect of the invention. The timeline shows a slow addition of the water phase until inversion of the phases occurs, determined by conductance measurements, whereupon rapid addition of the remainder of the water phase is effected.

The resultant composition is a blue white emulsion which leaves no residue on glass. Only a small amount of foaming occurs mostly during the rapid addition of the remainder of the water phase. Temperature of the mix was maintained at 70-75° C. during mixing but cooling was initiated immediately the addition of the water phase had been completed. The majority of particles reviewed under a microscope were much less than 1 µm in diameter. The composition remained stable at 3 days.

Figure 4:
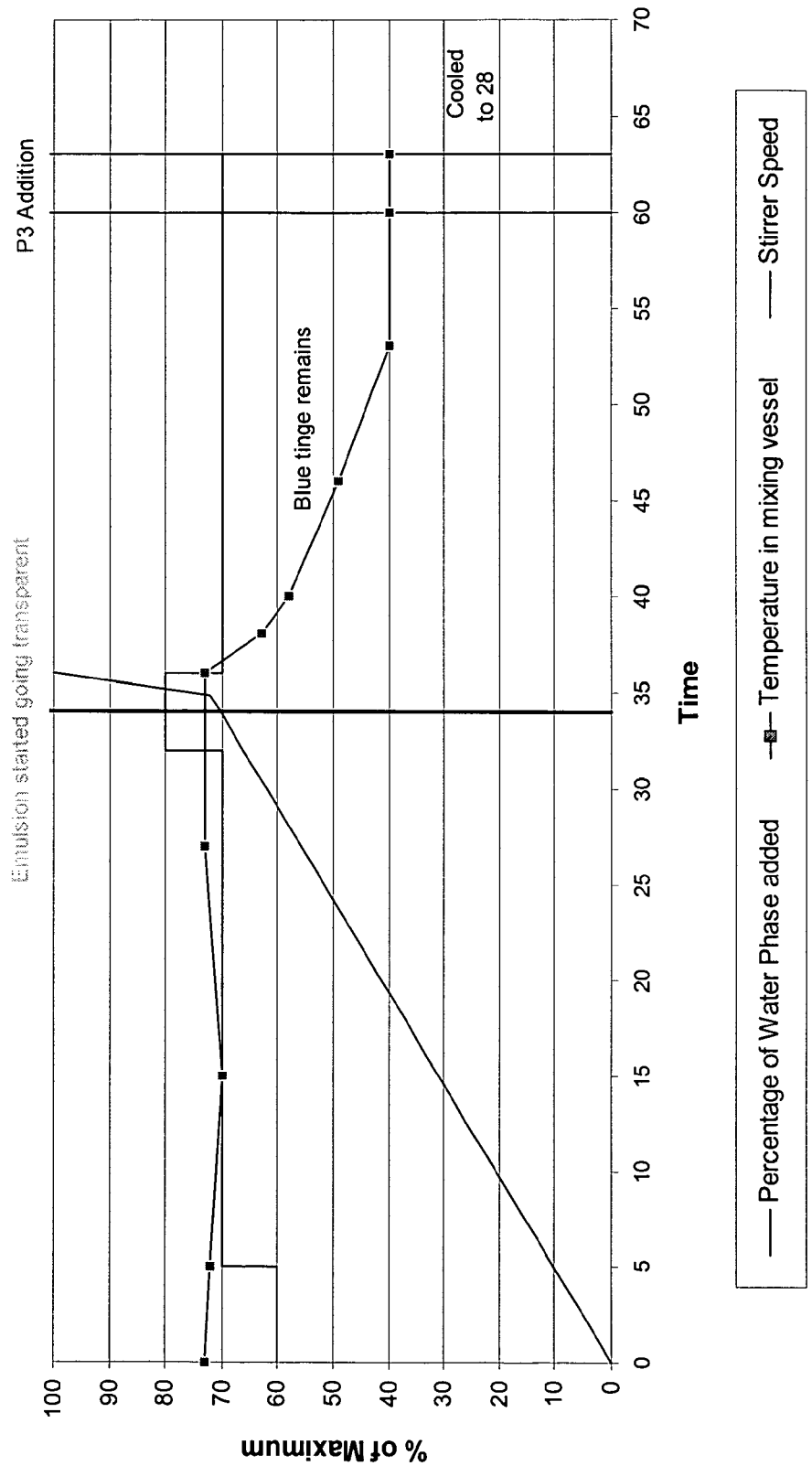
FIG. 4 is a graphical representation of the method depicted in the timeline of FIG. 3.

FIG. 4 is a graphical representation of the process of this example changing the rate of addition of the various components of the composition.

Example 10

Figure 5:
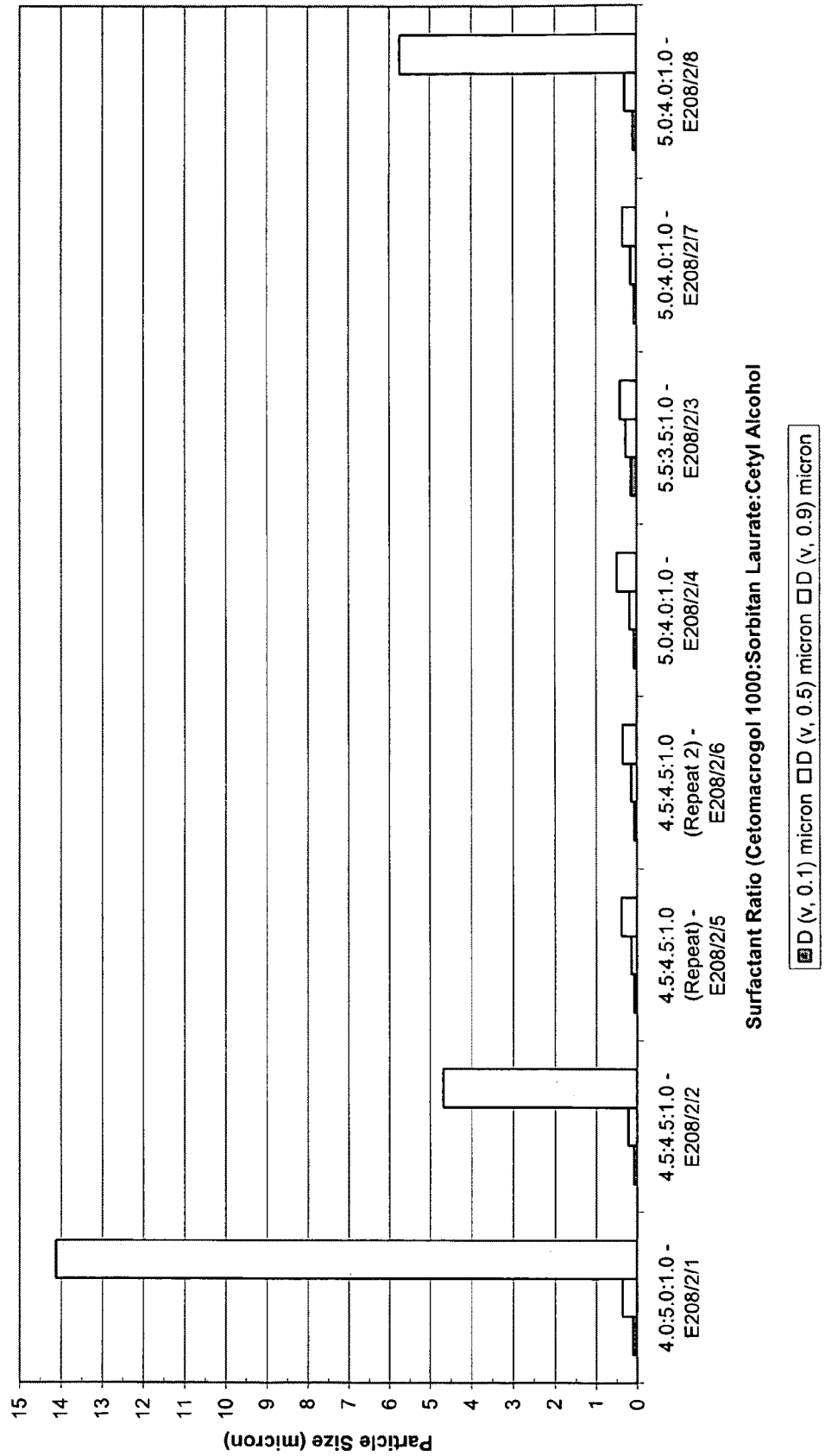
FIG. 5 shows the effect on particle size distribution of varying the ratio of surfactants in betamethasone valerate compositions according to the invention.

This example demonstrates the effect of varying the ratio of emulsifiers in one composition prepared according to an embodiment of the invention wherein the pharmaceutically active ingredient is betamethasone valerate and the emulsifiers are Ceteareth-20, sorbitan laurate and cetyl alcohol. It also shows the effect of varying the manner of addition of the water phase; either all at once, or in two separate stages, the first stage being added at a slower rate than the second stage. FIG. 5 shows the results of this example graphically. The acronym "BMV" is Betamethasone valerate.

The compositions E208/2/1—E208/2/8 are prepared as follows in accordance with differing preferred embodiments of the invention:

- E208/2/1—4.0:5.0:1.0 ratio of Ceteareth-20:sorbitan laurate:cetyl alcohol, all water phase added in one hit—heated to 81° C.
- E208/2/2—4.5:4.5:1.0 ratio of Ceteareth-20:sorbitan laurate:cetyl alcohol, all water phase added in one hit—heated to 82° C.
- E208/2/3—5.5:3.5:1.0 ratio of Ceteareth-20:sorbitan laurate:cetyl alcohol, all water phase added in one hit—heated to 94° C.
- E208/2/4—5.0:4.0:1.0 ratio of Ceteareth-20:sorbitan laurate:cetyl alcohol, all water phase added in one hit—heated to 84° C.
- E208/2/5—4.5:4.5:1.0 ratio of Ceteareth-20:sorbitan laurate:cetyl alcohol, all water phase added in one hit—heated to 92° C.
- E208/2/6—4.5:4.5:1.0 ratio of Ceteareth-20:sorbitan laurate:cetyl alcohol, all water phase added in one hit—heated to 78° C.
- E208/2/7—5.0:4.0:1.0 ratio of Ceteareth-20:sorbitan laurate:cetyl alcohol, water phase added in two portions (70/30 hot:cold) propylene glycol stirred when added—heated to 74° C.
- E208/2/8—5.0:4.0:1.0 ratio, of Ceteareth-20:sorbitan laurate:cetyl alcohol water phase added in two portions (70/30 hot:cold) propylene glycol not stirred when added-heated to 74° C.

This example shows that a microemulsion meeting the objects of the invention can be made at varying surfactant ratios.

Figure 6:
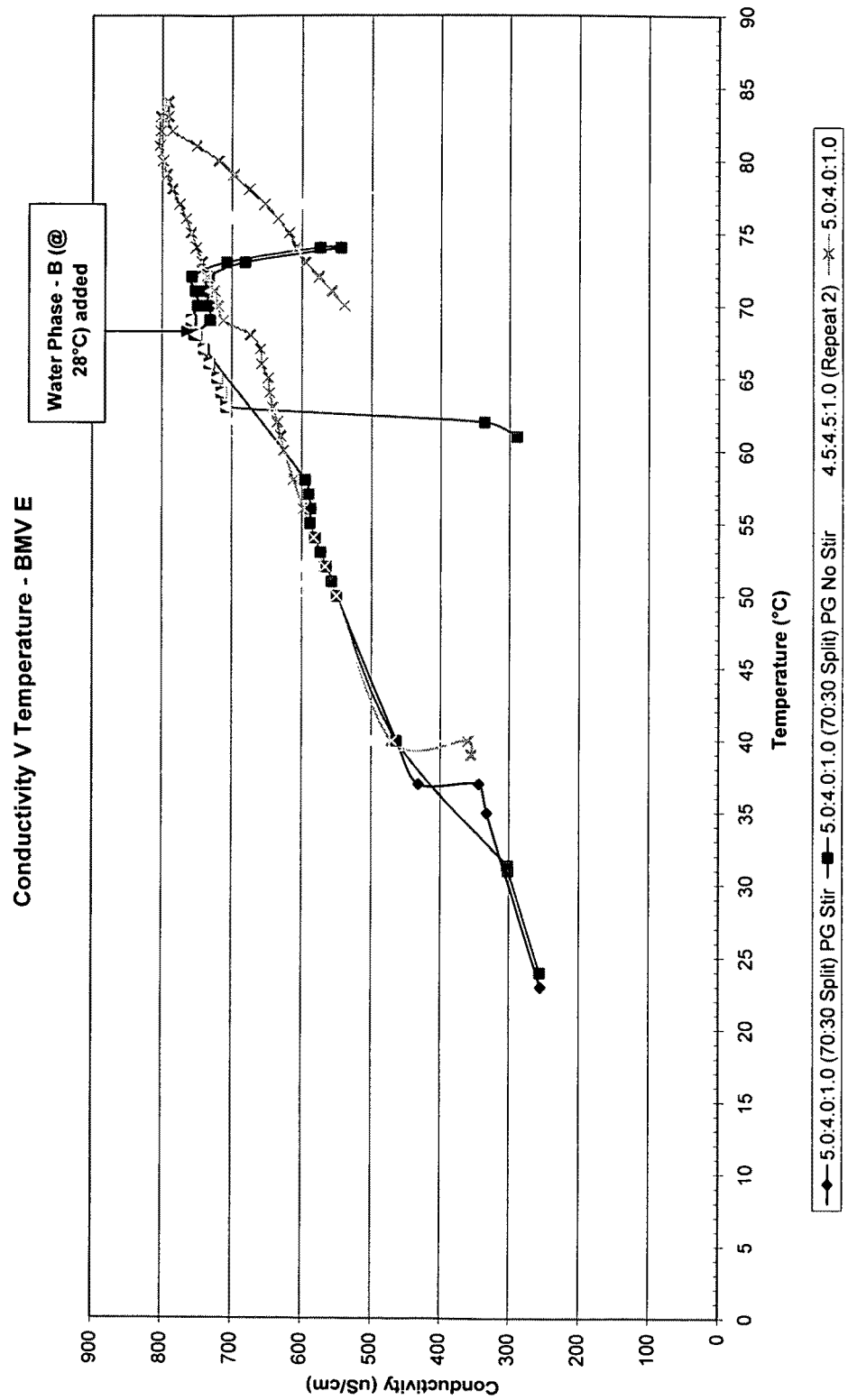
FIG. 6 shows the conductivity response from heating various compositions according to the invention to the assembly temperature, and then cooling them.

In order to determine the point at which a microemulsion is formed, conductance tests are recommended. The conductivity will drop dramatically immediately phase assembly occurs at the set point of the microemulsion. Utilising the compositions E208/2/7, E208/2/8, E208/2/6 and E208/2/4 (left to right across the key), FIG. 6 graphs conductivity of the compositions against the temperature of the water/oil phase mix and shows the conductivity response from heating to the assembly temperature and subsequent cooling and addition of active phase. The uppermost section, or assembly temperature range, of the conductivity plot demonstrates the trend that the set point of compositions according to the invention can be reduced by decreasing the relative proportion of hydrophilic surfactant in the surfactant system. The assembly temperature is also lowered when the water phase is split into two aliquots. It is postulated that splitting the water phase has the same effect as reducing the relative proportion of hydrophilic surfactant and subsequently lowering the assembly temperature for the microemulsion.

Example 11

This example demonstrates the effect on the appearance and particle size of varying the parameters of the processes hereinbefore described. Table 2 shows that the phase in which the surfactant is added, and the presence or absence of non-surfactant, amphiphilic substances in the composition prior to emulsification of the compositions, has an effect on the particle size of the composition. In the context of the example, it will be appreciated that the compositions meeting the objects of the invention are those wherein the water phase is added to the oil phase, Ceteareth-20 is present in the water phase, and the remaining surfactants are present in the oil phase, and wherein the addition of the non-surfactant amphiphilic components of the composition are added after emulsification of the composition at the phase assembly temperature. In this case, the composition appears to have acceptable stability, and a particle size of less than 0.2 µm.

TABLE 2

| | Surfactant addition | | | | | | |
|---|---|---|---|---|---|---|---|
| Process description | Ceteareth-20 | Sorbitan laurate | Cetyl alcohol | Polyol & Phenoxy ethanol addition | Appearance | Particle size (µm) | Comments |
| Water phase added to oil phase | Oil phase | Oil phase | Oil phase | Water phase (before emulsification) | White liquid | <20 | Creaming observed within 24 hours |
| Water phase added to oil phase | Split between oil phase and water phase | Oil phase | Oil phase | Water phase (before emulsification) | White liquid | <20 | Creaming observed within 24 hours |
| Water phase added to oil phase | Water phase | Oil phase | Oil phase | Water phase (before emulsification) | White liquid | <20 | Creaming observed within 24 hours |

TABLE 2-continued

| Process description | Surfactant addition | | | Polyol & Phenoxy ethanol addition | Appearance | Particle size (μm) | Comments |
|---|---|---|---|---|---|---|---|
| | Ceteareth-20 | Sorbitan laurate | Cetyl alcohol | | | | |
| Water phase added to oil phase | Water phase | Oil phase | Oil phase | Emulsion (after emulsification) | Bluish-white, translucent liquid | <0.2 | No creaming observed over several days |
| Oil phase added to water phase | Oil phase | Oil phase | Oil phase | Water phase (before emulsification) | White liquid | <20 | Creaming observed within 24 hours |
| Oil phase added to water phase | Water phase | Oil phase | Oil phase | Water phase (before emulsification) | White liquid | <20 | Creaming observed within 24 hours |

Example 12

In order to demonstrate the chemical and physical stability of compositions prepared according to the process of the invention compared to those of the prior art, the following tests were carried out. In the compositions prepared according to the process of the invention (12B) the polyol and/or alcohol are added in a third phase after emulsification and cooling of the oil in water emulsion formed in the first stage of the process. In the compositions prepared according to prior art processes (12A) the polyol and/or alcohol are added to the oil or water phase prior to emulsification and cooling of the composition. Table 3 shows the 6 month stability data associated with a composition according to Example 12A; a prior art type composition.

Example 12A

Prior Art

| Item No. | Ingredient | % w/w | % w/w without Propellant |
|---|---|---|---|
| | Part 1 | | |
| 1 | Clobetasol Propionate | 0.0475 | 0.050 |
| 2 | Snow White Petrolatum | 7.50 | 7.895 |
| 3 | Lt Mineral Oil (Drakeol 5) | 5.00 | 5.263 |
| 4 | Isopropyl Myristate | 7.50 | 7.895 |
| 5 | ST-Cyclomethicone 5-NF | 5.00 | 5.263 |
| 6 | Cetomacrogol 1000 BP | 6.50 | 6.842 |
| 7 | Cetyl Alcohol | 2.00 | 2.105 |
| 8 | Sorbitan Laurate (Crill 1) | 1.50 | 1.579 |
| | Part 2 | | |
| 9 | Purified water | 38.7525 | 37.803 |
| 10 | Citric Acid, anhydrous | 0.04 | 0.042 |
| 11 | Potassium Citrate, monohydrate | 0.16 | 0.168 |
| 12 | Propylene Glycol | 20.00 | 21.053 |
| 13 | Phenoxyethanol | 1.00 | 1.053 |
| | Part 3 | | |
| 14 | Propellant P70 | 5 | |
| | TOTAL | 100.00 | 100.00 |

Preparation:
1. Part 1 preparation: Add Items 2 to 8 into the mixing vessel. Heat to 60° C. and stir to combine. Maintain temperature before adding Clobetasol Propionate. Stir until dissolved then increase the temperature to 80-85° C. in preparation for part 2 addition.
2. Part 2 preparation: Add items 9 to 13 to a mixing vessel and heat to 80-85° C. with stirring until a clear solution is formed.
3. Emulsification: Stir part 1 well (without introducing air) then add part 2. Initially add part 2 at a slower rate. During part 2 addition, a period of higher viscosity will occur that may require an increased stirring speed, for a short time, to ensure thorough mixing.
4. Homogenisation: Stir and cool the emulsion to 40° C. (cool at a reasonably fast rate). Homogenise the emulsion if the average particle size is >2.5 μm or the maximum particle size is >15 μm. Stir cool the emulsion to 25° C.

TABLE 3

| Storage temperature ° C. | Test time point | Clobetasol % | % of T = 0 | Phenoxy-ethanol % | % of T = 0 | Weight loss (g) | Pressure psig @ 25° C. | Foam pH @ 25° C. | Re-disp. at 10° C. | Re-disp. at 15° C. | Foam at 15° C. | Foam at 25° C. | Foam at 35° C. | Spay Rate gs$^{-1}$ 21° C. |
|---|---|---|---|---|---|---|---|---|---|---|---|---|---|---|
| | Initial | 0.0502 | — | 1.060 | — | — | 44 | 6.04 | — | — | 0.5 | 1.0 | — | 4.2 |
| 5° C. | 1 month | 0.0499 | 99.4 | 1.051 | 99.2 | | | | | | | | | |
| | 2 months | 0.0500 | 99.6 | 1.050 | 99.1 | | | | | | | | | |
| | 3 months | 0.0501 | 99.8 | 1.053 | 99.3 | | | | | | | | | |
| | 6 months | 0.0502 | 100.0 | 1.046 | 98.7 | | | | | | | | | |
| | 9 months | | | | | | | | | | | | | |
| | 12 months | | | | | | | | | | | | | |
| 25° C. | 3 months | 0.0502 | 100.0 | 1.047 | 98.7 | 0.023 ± 0.009 | 43 | 6.07 | 5 | 4 | 0.5 | 1.0 | 1.5 | 4.2 |
| | 6 months | 0.0495 | 98.6 | 1.043 | 98.4 | 0.043 ± 0.007 | 43 | 6.05 | 6 | 5 | 0.5 | 0.5 | 1.5 | 2.9 |
| | 9 months | | | | | | | | | | | | | |
| | 12 months | | | | | | | | | | | | | |
| 30° C. | 2 months | 0.0498 | 99.1 | 1.045 | 98.5 | 0.024 ± 0.006 | 44 | 6.03 | 5 | 3 | 0.5 | 1.0 | — | 4.3 |
| | 3 months | 0.0499 | 99.3 | 1.045 | 98.6 | 0.030 ± 0.008 | 45 | 6.12 | 6 | 5 | 0.5 | 1.0 | 1.5 | 3.1 |

TABLE 3-continued

| Storage temperature ° C. | Test time point | Clobetasol % | % of T = 0 | Phenoxy-ethanol % | % of T = 0 | Weight loss (g) | Pressure psig @ 25° C. | Foam pH @ 25° C. | Re-disp. at 10° C. | Re-disp. at 15° C. | Foam at 15° C. | Foam at 25° C. | Foam at 35° C. | Spay Rate gs⁻¹ 21° C. |
|---|---|---|---|---|---|---|---|---|---|---|---|---|---|---|
| | 6 months | 0.0496 | 98.8 | 1.040 | 98.1 | 0.076 ± 0.007 | 42 | 6.07 | 6 | 5 | 0.5 | 0.5 | 1.5 | 4.4 |
| | 9 months | | | | | | | | | | | | | |
| | 12 months | | | | | | | | | | | | | |
| 40° C. | 1 month | 0.0497 | 98.9 | 1.046 | 98.6 | 0.039 ± 0.006 | 43 | 6.04 | 5 | 4 | 0.5 | 1.0 | — | 4.6 |
| | 2 months | 0.0496 | 98.7 | 1.045 | 98.6 | 0.057 ± 0.005 | 43 | 6.03 | 6 | 5 | 0.5 | 1.0 | — | 4.1 |
| | 3 months | 0.0496 | 98.8 | 1.043 | 98.3 | 0.083 ± 0.007 | 45 | 6.13 | 6 | 5 | 0.5 | 1.0 | 1.5 | 4.6 |
| | 6 months | 0.0490 | 97.5 | 1.045 | 98.5 | 0.162 ± 0.011 | 42 | 6.06 | 6 | 6 | 0.5 | 0.5 | 1.5 | 4.2 |

Example 12B

| Item No. | Ingredient | % w/w | % w/w without Propellant |
|---|---|---|---|
| | Part 1 | | |
| 1 | Snow White Petrolatum | 7.50 | 7.895 |
| 2 | Lt Mineral Oil (Drakeol 5) | 5.00 | 5.263 |
| 3 | Isopropyl Myristate | 7.50 | 7.895 |
| 4 | ST-Cyclomethicone 5-NF | 5.00 | 5.263 |
| 5 | Cetyl Alcohol | 1.00 | 1.053 |
| 6 | Sorbitan Laurate (Crill 1, USA) | 4.50 | 4.737 |
| | Part 2 (Part 2A = 70%, Part 2B = 30%) | | |
| 7 | Purified water | 38.7525 | 40.792 |
| 8 | Cetomacrogol 1000 BP | 4.50 | 4.737 |
| 9 | Citric Acid, anhydrous | 0.040 | 0.042 |
| 10 | Potassium Citrate, monohydrate | 0.160 | 0.168 |
| | Part 3 | | |
| 11 | Propylene Glycol | 20.00 | 21.053 |
| 12 | Phenoxyethanol | 1.00 | 1.053 |
| 13 | Clobetasol Propionate | 0.0475 | 0.050 |
| | Part 4 | | |
| 14 | Propellant P70 | 5 | |
| | TOTAL | 100.00 | 100.00 |

Preparation:

1. Part 1 preparation: Add Items 1 to 6 into the mixing vessel. Heat to 60-80° C. and stir to combine. Maintain temperature before adding Part 2A.
2. Part 2 preparation: Add Item 7 (Water) at room temp, Item 9 (Citric acid, anhydrous) and Item 10 (Potassium Citrate, monohydrate) to a suitably sized vessel. Stir well and add all of Item 8 (Cetomacrogol 1000 BP). Heat to a maximum of 50° C. until the Cetomacrogol has completely dissolved (above 50° C. the cetomacrogol melts and will clump to form a large mass).
3. Part 2 separation: Perform a weight check on part 2 then split into
   Part 2A—containing 70% of Part 2
   Part 2B—containing 30% of Part 2
   Cool part 2B to 20-30° C. (ideally 20-25° C.).
4. Part 2A addition: Add part 2A to the mixing vessel. Part 2A may be added immediately after dissolving the Cetomacrogol when hot, or if it was previously prepared and had cooled to room temp.
5. Heat the mixing vessel to at least 80-85° C. (part 1+part 2A), with good mixing and hold for 10 min When measuring the conductivity, this will be <100 μS/cm, if not, increase the temperature.
   Allow the mixing vessel to slowly cool to 73.0° C. When approaching the target temperature (73.0° C.) the cooling rate should be no more than 1° C. per min. This should correspond to the maximum clarity of the emulsion. It is also the point where ΔConductivity changes from a large negative value to almost constant zero.
6. Addition of Part 2B: When the mixing vessel reaches 73.0° C., pump in part 2B (which is at 25° C.) and immediately begin cooling the mixing vessel. Addition of part 2B should be completed within 90 s. The temperature of the mixture should be about 60° C. at the completion of part 2B addition.
7. Addition of Part 3: Stir and cool the mixing vessel to 35-40° C. Part 3 should be previously prepared by adding Items 11 to 13 into a suitable vessel and heating until the Clobetasol is dissolved. Cool Part 3 to <30° C. after the Clobetasol has dissolved and add to the mixing vessel at a rate to take at least 5-10 min.
8. Stir cool the mixing vessel to 25-30° C. (25° C. preferable). Perform a weight check. Base emulsion should be maintained at 20-25° C. before filling. Base emulsion should remain homogeneous for at least 48 hr without stirring.

Table 4 shows 3 month stability data associated with a composition according to Example 12B, a composition prepared in accordance with one form of the invention.

TABLE 4

| Storage temperature ° C. | Test time point | Clobetasol Propionate % | % of T = 0 | Phenoxy-ethanol % | % of T = 0 | Weight loss (g) | Pressure psig @ 25° C. | Foam pH @ 25° C. | Re-disp. at 5° C. | Foam at 15° C. | Foam at 25° C. | Foam at 35° C. | Package interaction |
|---|---|---|---|---|---|---|---|---|---|---|---|---|---|
| | Initial | 0.0497 | — | 1.034 | — | — | 31 | 6.20 | — | 3.0 | 1.5 | 2.0 | — |
| 25° C. | 3 months | 0.0491 | 98.8 | 1.0409 | 100.7 | 0.03 | 30 | 6.23 | 1 | 4.5 | 2.0 | 1.0 | Lining - no change. Gasket, spring, valve cup - no change, valve body and stem-Slightly yellowed. No signs |

TABLE 4-continued

| Storage temperature °C. | Test time point | Clobetasol Propionate % | % of T = 0 | Phenoxy-ethanol % | % of T = 0 | Weight loss (g) | Pressure psig @ 25° C. | Foam pH @ 25° C. | Re-disp. at 5° C. | Foam at 15° C. | Foam at 25° C. | Foam at 35° C. | Package interaction |
|---|---|---|---|---|---|---|---|---|---|---|---|---|---|
| | 6 months | | | | | | | | | | | | of attack on scratch (clean and bright) |
| 40° C. | 1 month | 0.0491 | 98.8 | 1.0288 | 99.5 | 0.01 | 28 | 6.21 | 1 | 1.5 | 1.0 | 1.5 | Lining - no change. Gasket, spring, valve cup, valve body and stem-no change. No signs of attack on scratch (clean and bright) |
| | 3 months | 0.0487 | 98.0 | 1.0262 | 99.2 | 0.06 | 30 | 6.20 | 1 (10° C.) | 4.0 | 1.5 | 2.5 | Lining - no change. Gasket, spring, valve cup - no change, valve body and stem-Slightly yellowed. No signs of attack on scratch (clean and bright) |
| | 6 months | | | | | | | | | | | | |

Comparing Tables 3 and 4 it can be seen that the active ingredient, clobetasol propionate and the preservative, phenoxyethanol, which are both routinely analysed, are not affected by the physical form of the emulsion (i.e. prior art versus a composition according to the invention).

Example 13

The physical stability of the formulation prepared according to the methods of the invention has been confirmed using a Turbiscan Transmission Plot which shows that after 4 days, the dispersed phase is homogenously distributed throughout the sample meaning that no phase separation has occurred.

| | Surfactant Ratio (Ceteareth-20:Sorbitan Laurate:Cetyl Alcohol) | | | | |
|---|---|---|---|---|---|
| | 4.0:5.0:1.0 | 4.5:4.5:1.0 | 5.0:4.0:1.0 | 5.5:3.5:1.0 | 6.0:3.0:1.0 |
| Part 1 | | | | | |
| Petrolatum | 5.00 | 5.00 | 5.00 | 5.00 | 5.00 |
| Mineral Oil | 5.00 | 5.00 | 5.00 | 5.00 | 5.00 |
| Isopropyl Myristate | 5.00 | 5.00 | 5.00 | 5.00 | 5.00 |
| Cyclomethicone | 5.00 | 5.00 | 5.00 | 5.00 | 5.00 |
| Cetyl Alcohol | 1.00 | 1.00 | 1.00 | 1.00 | 1.00 |
| Sorbitan Laurate | 5.00 | 4.50 | 4.00 | 3.50 | 3.00 |
| Part 2 | | | | | |
| Water | 58.80 | 58.80 | 58.80 | 58.80 | 58.80 |
| Ceteareth-20 | 4.00 | 4.50 | 5.00 | 5.50 | 6.00 |
| Citric Acid | 0.12 | 0.12 | 0.12 | 0.12 | 0.12 |
| Potassium Citrate | 0.08 | 0.08 | 0.08 | 0.08 | 0.08 |
| Part 3 | | | | | |
| Propylene Glycol | 5.00 | 5.00 | 5.00 | 5.00 | 5.00 |
| Phenoxy Ethanol | 1.00 | 1.00 | 1.00 | 1.00 | 1.00 |
| Part 4 | | | | | |
| Hydrocarbon Propellant P70 | 5.00 | 5.00 | 5.00 | 5.00 | 5.00 |
| Total | 100.00 | 100.00 | 100.00 | 100.00 | 100.00 |
| Turbiscan @ >4 days | Creaming | Creaming | Slight Creaming | Stable | Stable |

Example 14

Figure 7:
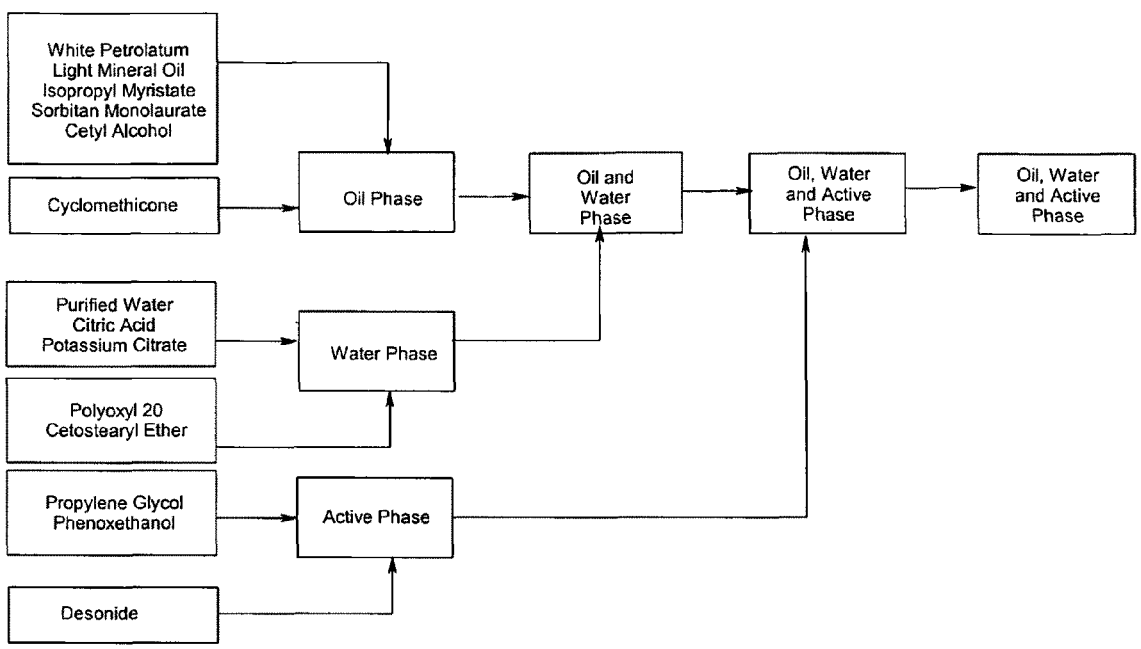
FIG. 7 is a schematic flow diagram of the process used to produce the formulation subject of the clinical trials described in Example 14.
Figure 8:
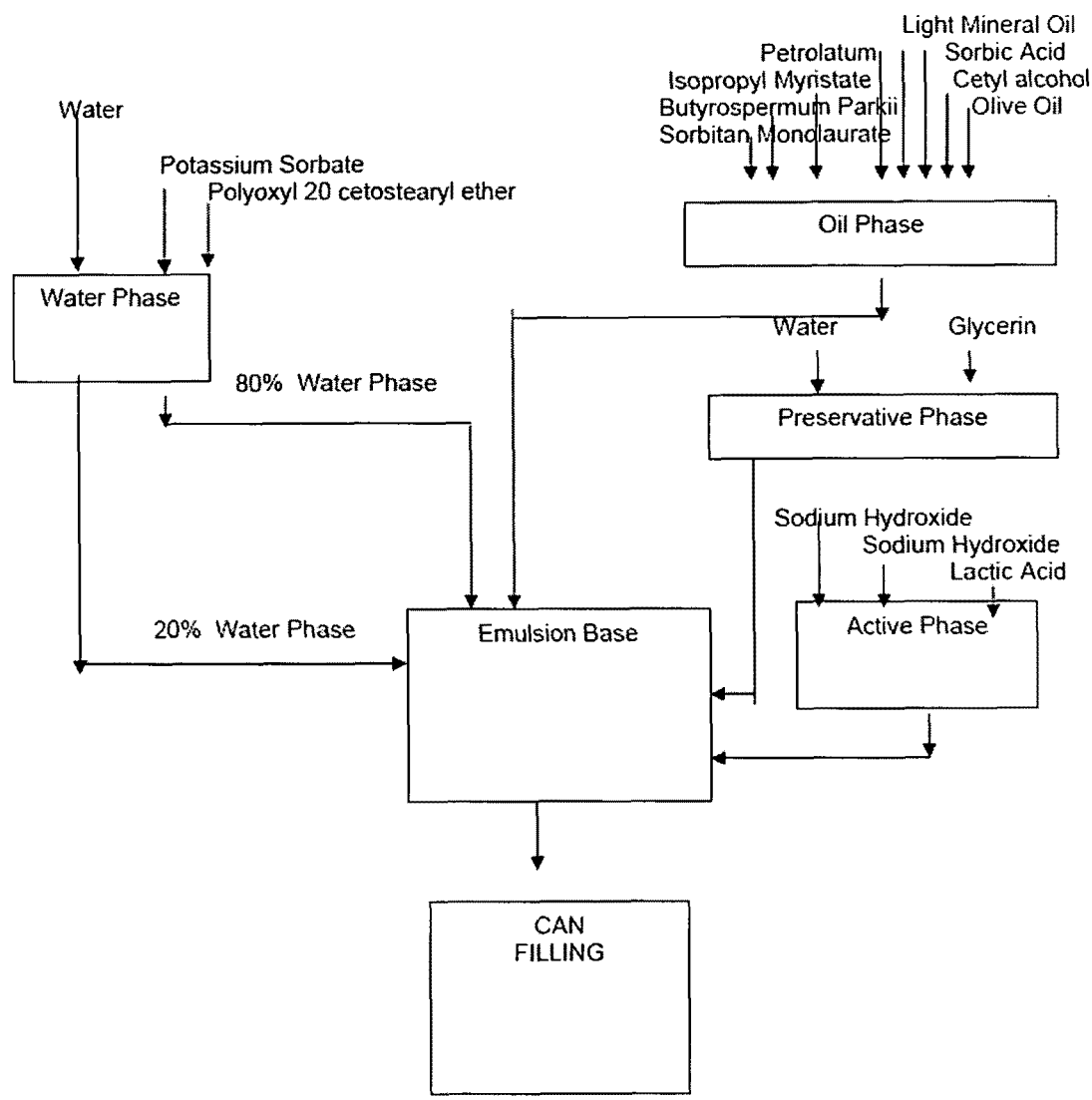
FIG. 8 is a schematic flow diagram showing one preferred embodiment of the invention in which 0.2% and 10% lactic acid sub-micron emulsion is prepared.
Figure 9:
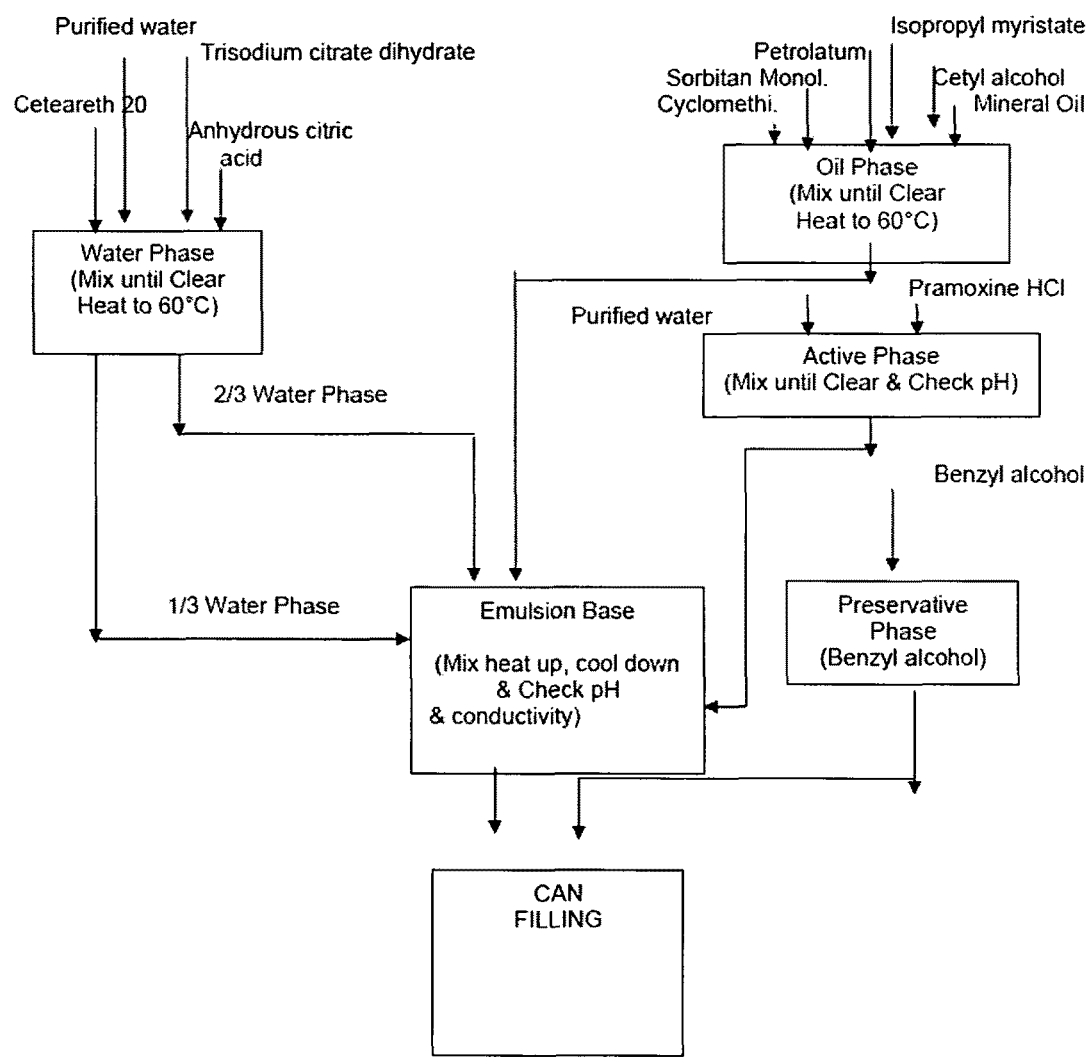
FIG. 9 is a schematic flow diagram showing one preferred embodiment of the invention in which 1% pramoxine sub-micron emulsion foam is prepared.

Using the formulation set out below and made using the procedure illustrated in FIG. 7, a phase II clinical trial was conducted as described.

|  | 17% PG/pH 5 % w/w |
|---|---|
| Part 1 |  |
| White Petrolatum | 5.26 |
| Light Mineral Oil | 5.26 |
| Isopropyl Myristate | 10.53 |
| Cyclomethicone | 2.63 |
| Cetyl Alcohol | 1.05 |
| Sorbitan Monolaurate | 4.74 |
| Part 2 |  |
| Purified Water | 46.58 |
| Polyoxyl 20 Cetostearyl Ether | 4.74 |
| Citric Acid Anhydrous | 0.08 |
| Potassium Citrate | 0.13 |
| Part 3 |  |
| Propylene Glycol | 17.90 |
| Phenoxy Ethanol | 1.05 |
| Desonide (micronized) | 0.05 |
| Emulsion concentrate Total | 100.00 |

The randomized phase II clinical trial involved 106 patients demonstrating mild to moderate atopic dermatitis who underwent a 4 week treatment and were followed up three weeks subsequently. Patients aged 3 months to 17 years were administered the above composition formulated as a foam in a ratio of 2:1 (desonide composition:vehicle absent desonide). The primary endpoints of the study were determined to be as follows:

Investigator's Static Global Assessment; clear (0) or almost clear (1), and
Erythema; 0 or 1, and
Induration/Papulation; 0 or 1, and
ISGA; minimum improvement of 2 grades.
There were multiple secondary endpoints.

The Part 2 results showed that where the primary endpoint was validated, there was a 53% response rate in patients treated with the desonide formulation and a 12% response rate in patients treated with the vehicle lacking the active agent desonide (placebo). The response rate to the placebo was as expected. The response rate to the desonide formulation was nearly double the expected rate (53% versus 27%). The formulations according to the invention show surprising and unexpected advantages over the expected response.

Example 15

A 0.12% betamethasone valerate sub-micron emulsion formulation was prepared to demonstrate the ability to dissolve a pharmaceutically active ingredient in the oil phase. The following formulation was prepared.

| Item No. | Ingredient | Trade Name |  |
|---|---|---|---|
| 1 | Octyl dimethyl PABA | Escalol 507 | 10.00 |
| 2 | Betamethasone Valerate | BMV | 0.12 |
| 3 | Mineral Oil | Drakeol 9 | 10.00 |
| 4 | Sorbitan Laurate | Crill 1 | 4.00 |

-continued

| Item No. | Ingredient | Trade Name |  |
|---|---|---|---|
| 5 | Ceteareth-20 | Cetomacrogol 1000BP | 5.00 |
| 6 | Cetyl Alcohol | Cetyl Alcohol | 1.00 |
| 7 | Purified Water | Water | 64.18 |
| 8 | Citric Acid | Citric Acid Anhydrous | 0.11 |
| 9 | Potassium Citrate | Potassium Citrate | 0.09 |
| 10 | Phenoxyethanol | Phenoxyethanol | 0.50 |
| 11 | P70 | Propellent 70 | 5.00* |
|  |  | Total: | 100.00 |

The formulation was prepared according to the following protocol:

Combine items 1 and 2. Stir until completely dissolved.
Add items 3, 4, 5 and 6. Heat to 60° C. and stir until dissolved.
In a separate beaker, combine items 7, 8, 9 and 10. Stir until dissolved.
With stirring add 70% of the water phase to the warm, clear oil phase.
Continue stirring and heating while recording the temperature and the conductivity.
Continue heating and stirring to just past the assembly temperature (approx. 74° C.). Remove the emulsion from heat and place on a cool stirrer.
Continue stirring and add the remaining water phase at the temperature when conductivity is at a maximum (approx. 70-72° C.).
Stir cool to 30° C. Top up with water to account for evaporative loss.
Test pH and adjust to pH 4 (if required)

The physical characteristics the formulation is summarised as follows:

| Formulation | SME |
|---|---|
| Appearance | Translucent, water thin emulsion |
| pH (@RT) | 3.97 |
| DLS mean diameter (nm) | 64.0 |
| SPOS (% volume > 0.5 um) | 0.109 |

Example 16

| Item No. | Formulation No | F743/1/4 | F743/1/6 |
|---|---|---|---|
|  | Part 1 - Oil phase |  |  |
| 1 | White Petrolatum, USP | 5.0 | 5.0 |
| 2 | Light Mineral Oil, NF | 5.0 | 5.0 |
| 3 | Isopropyl Myristate, NF | 5.0 | 5.0 |
| 4 | Olive Oil, NF | 1.0 | 1.0 |
| 5 | *Butyrospermum Parkii* (Shea Butter) | 2.0 | 2.0 |
| 6 | Sorbic Acid, NF | 0.05 | 0.05 |
| 7 | Cetyl Alcohol, NF | 0.75 | 0.75 |
| 8 | Sorbitan Monolaurate, NF | 5.63 | 5.63 |
|  | Part 2 - Water phase |  |  |
| 9 | Water | 36.09 | 36.09 |
| 10 | Potassium Sorbate, NF | 0.05 | 0.05 |
| 11 | Polyoxyl 20 cetostearyl ether, NF | 5.63 | 5.63 |
|  | Part 3 - Humectant phase |  |  |
| 12 | Water | 23.4 | 3.8 |
| 13 | Glycerin, USP | 10.0 | 10.0 |

-continued

| Item No. | Formulation No | F743/1/4 | F743/1/6 |
|---|---|---|---|
| | Part 4 - Lactate phase | | |
| 14 | Water | 0.13 | 6.67 |
| 15 | Sodium Hydroxide pure, NF | 0.044 | 2.22 |
| 16 | Lactic Acid (90% solution), NF | 0.22 | 11.11 |
| | TOTAL | 100.00 | 100.00 |

Example 16 shows a surfactant ratio of Polyoxy 20 cetostearyl ether:sorbitan monolaurate:cetyl alcohol of 7.5:7.5:1.0.

Preparation:

1. Part 1 preparation: Add Items 1 to 8 into the main mixing vessel. Heat to 50-70° C. and stir to combine. The temperature may be maintained or allowed to cool (e.g. if prepared on a previous day) prior to adding Part 2A, depending on convenience.
2. Part 2 preparation: Add Item 9 (water) and Item 10 (potassium sorbate) to a suitably sized vessel at room temperature and mix until dissolved. Add Item 11 (Cetomacrogol 1000 BP) with stirring and continue to stir until completely dissolved. This phase may be heated up to a maximum of 50° C. to assist Cetomacrogol dissolution (above 50° C. the cetomacrogol melts and may clump together, forming a large mass).
3. Perform a weight check on Part 2 then divide into two portions:
   Part 2A—containing 80% of Part 2, and
   Part 2B—containing 20% of Part 2.
   Cool Part 2B to 20-30° C. (ideally 20-25° C.).
4. Part 2A addition: Add Part 2A to the mixing vessel (high addition rate is OK). The temperature of Part 2A before addition is not critical. Part 2A may be added immediately after dissolving the Cetomacrogol when hot, or if it was previously prepared and had cooled to room temp.
5. Heat the mixing main vessel containing Part 1 and 2A to at least 80-85° C. with good mixing without aeration and hold for 10 min (just to ensure uniformity).
6. Allow the mixing vessel to slowly cool to the phase assembly temperature (PAT) of 71.0-74.0° C. When approaching the PAT the cooling rate should be no more than 1° C. per min. The PAT should correspond to the maximum clarity of the emulsion.
7. Addition of Part 2B: When the mixing vessel reaches 71.0-74.0° C., pump in Part 2B (which is at 25° C.) and immediately begin cooling the mixing vessel. Addition of Part 2B must be completed within 60 s (faster pumping rates may be used). Therefore, larger batches require faster pump speeds. The temperature of the mixture should decrease to about 60° C. at the completion of Part 2B addition (i.e. at least 10° C. decrease within 1 min). To ensure adequate cooling for large batches, Part 2B may be cooled to <20° C. If the mixing vessel cools to <71.0° C. before Part 2B can be added, the mixing vessel may be reheated to 74.0° C. before the addition of Part 2B. During this second heating it is not necessary to reach 80° C. This example suggests that it is better to be at the upper end of the 71-74° C. range for the Part 2B addition.
8. Addition of Part 3: Part 3 should be previously prepared by adding Items 12 (water) and 13 (glycerin) into a suitable vessel and mixing. Stir and cool the main mixing vessel to <30° C. and ensure thorough mixing without aeration. Add Part 3 to the main mixing vessel at a slow rate that takes at least 5 min to complete. (Note: if the Part 3 addition is too fast, or the mixing too slow during Part 3 addition, larger oil-drops can form, which can subsequently separate to the top of the emulsion on standing)
9. Addition of Part 4: Part 4 should be previously prepared by first dissolving Item 15 (sodium hydroxide) into Item 14 (water) in a suitable vessel, whilst mixing. This solution is cooled to room temperature. Item 16 (lactic acid) is added to a separate vessel and stirred gently. Whilst stirring Item 16, the caustic solution (comprising Items 14 and 15) is slowly added, mixed until uniform and cooled to room temperature. Add Part 4 to the main mixing vessel (with thorough mixing) at a slow rate that takes at least 5 min to complete (Note: if the Part 4 addition is too fast, or the mixing too slow during Part 4 addition, larger oil-drops can form, which can subsequently separate to the top of the emulsion on standing).
10. Stir cool the mixing vessel to 25-30° C. (25° C. preferable). Perform a weight check. The base emulsion should be maintained at 20-25° C. before filling. The base emulsion should remain homogeneous for at least 48 hr without stirring.

Example 17

| | Part 1 - Oil | |
|---|---|---|
| 1 | White Petrolatum, USP | 5.0 |
| 2 | Light Mineral Oil | 5.0 |
| 3 | Isopropyl Myristate, NF | 5.0 |
| 4 | Olive Oil, NF | 1.0 |
| 5 | *Butyrospermum Parkii* (Shea Butter) | 2.0 |
| 6 | Sorbic Acid, NF | 0.05 |
| 7 | Cetyl Alcohol, NF | 0.75 |
| 8 | Sorbitan Monolaurate, NF | 5.63 |
| | Part 2 - Water | |
| 9 | Water | 35.09 |
| 10 | Potassium Sorbate, NF | 0.05 |
| 11 | Polyoxyl 20 cetostearyl ether, NF | 5.63 |
| | Part 3 - Humectant phase | |
| 12 | Water | 6.64 |
| 13 | Glycerin, USP | 10.0 |
| | Part 4 - Lactate phase | |
| 14 | Ammonium lactate (70%) solution | 17.16 |
| | TOTAL | 100.00 |

Example 17 shows a surfactant ratio of Polyoxy 20 cetostearyl ether:sorbitan monolaurate:cetyl alcohol of 7.5:7.5:1.0.

Preparation:

The formulation of Example 17 is prepared according to the preparation method described in Example 16 except that Part 4, the Lactate phase, comprises a 70% ammonium lactate solution.

Example 18

| Ingredient | % w/w (without Preservative) | % w/w (with Preservative) |
| --- | --- | --- |
| Part 1 (Oil Phase) | | |
| Petrolatum | 5.00 | 5.00 |
| Isopropyl myristate | 5.00 | 5.00 |
| Mineral oil | 5.00 | 5.00 |
| Cyclomethicone | 5.00 | 5.00 |
| Cetyl alcohol | 0.80 | 0.80 |
| Sorbitan monolaurate | 4.00 | 4.00 |
| Total Part 1 | 24.80 | 24.80 |
| Part 2 (Water Phase) | | |
| Purified water | 58.96 | 57.46 |
| Trisodium citrate dihydrate | 0.20 | 0.20 |
| Anhydrous citric acid | 0.04 | 0.04 |
| Polyoxyl 20 cetostearyl ether | 5.00 | 5.00 |
| Total Part 2 | 64.20 | 62.70 |
| Part 3 (API Phase) | | |
| Purified Water | 10.00 | 10.00 |
| Pramoxine HCl | 1.00 | 1.00 |
| Total Part 3 | 11.00 | 11.00 |
| Part 4 (Preservative Phase) | | |
| Benzyl alcohol | 0.00 | 1.50 |
| Total Part 4 | 0.00 | 1.50 |
| Hydrocarbon propellant AP70 | | |
| Total (Parts 1 to 4) | 100.000 | 100.000 |
| Aerosol Base Fill Weight (g) | 46.25 | 46.25 |
| Propellant Fill Weight (g) | 3.75 | 3.75 |
| Total Fill Weight (g) | 50.00 | 50.00 |

Example 18 shows a surfactant ratio of Polyoxy 20 cetostearyl ether:sorbitan monolaurate:cetyl alcohol of 6.25:5.0:1.0.

Preparation:
1. Part 1 Preparation: Petrolatum, Isopropyl myristate, Mineral oil, Cyclomethicone, Cetyl alcohol and Sorbitan Monolaurate are added to a suitable stainless steel container at ambient temperature and mixed, with gentle heating, until a single-phase solution is formed.
2. Part 2 Preparation: Purified water, Anhydrous citric acid, Trisodium citrate dihydrate and Polyoxyl 20 cetostearyl ether are added to a suitable stainless steel container at ambient temperature and mixed until a clear, colorless solution is formed.
3. Part 3 Preparation: Pramoxine HCl and Purified water are added to a suitable stainless steel container at ambient temperature and mixed until a clear, colorless solution is obtained.
4. Part 4 Preparation: Benzyl Alcohol only.
5. Heat Part 1—Oil Phase to 60° C. whilst stirring.
6. Heat Part 2—Water phase to 60° C. whilst stirring.
7. In a separate vessel, with cooling and heating capabilities, transfer all of the Oil Phase and ⅔ of the Water Phase.
8. Heat the mixture whilst stirring and monitor temperature and conductivity. Continue until the conductivity reaches the plateau (around 1200 micro Siemens) at ~65C.
9. With additional heating, the conductivity will start to decrease slowly. At this point (i.e. the phase assembly temperature where the Sub-micron Emulsion (SME) is formed) add the remaining ⅓ of the water phase (at a temperature between room temperature and 60° C.).
10. Start cooling the SME mixture immediately. The conductivity will decrease with the addition of the water phase (to ~1400 micro Siemens) and will remain constant until the mixture is cooled down to ambient temperature.
11. The API Phase is added to the SME mixture at ambient temperature and mixed thoroughly. Conductivity will increase to ~2350 micro Siemens.
12. Perform an in-process test to confirm the pH of the Aerosol Base.
13. Check Aerosol Base visually for homogeneity and translucence.

Aerosol Filling and Crimping:

The aerosol base is filled into 35×125 mm PAM 8460 lined aluminum aerosol cans. When filling the composition with preservative system, the aerosol base and the benzyl alcohol are added in two separate portions. The inverted-use valves are inserted and the package is vacuum crimped and subsequently gassed with hydrocarbon propellant AP70. Cans are leak tested, by immersion in a 55-58° C. water bath, then cooled to ambient temperature and shaken briefly to mix the aerosol container's contents.

Example 19

This example demonstrates the stability of the 1% pramoxine HCl foam formulations of Example 18.

Foam Quality:

The foam has been developed primarily for use at room temperature (i.e. approx. 20° C.) and thus the foam quality is best at this temperature. As the foam is also likely to be dispensed at other temperatures, the foam quality was evaluated following storage at 40° C., using SOP 75 (SRA SOP NO. 75.04—Appearance of Emollient Foam (Revision 10 Dec. 2007), at two typical extremes in temperature (i.e. 100 and 30° C.).

Figure 10:
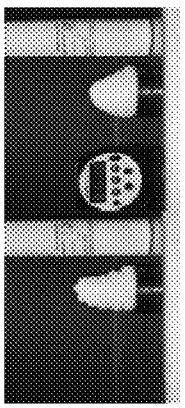
FIG. 10 is a table showing the foam quality of a formulation according to one preferred embodiment of the invention in which unpreserved 1% pramoxine semi-micron foam is evaluated at two typical extreme temperature of 10° and 30° C.
Figure 11:
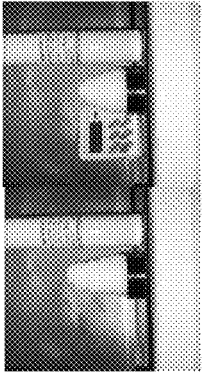
FIG. 11 is a table showing the foam quality of a formulation according to one preferred embodiment of the invention in which preserved 1% pramoxine semi-micron foam is evaluated at two typical extreme temperature of 10° and 30° C.

The results are presented in the tables of FIGS. 10 and 11. In conclusion, the unpreserved foam (Formula 692-15-21 in FIG. 10) collapses in size (after 6 months storage, test at 30° C.) only approximately 30% after 1 minute, and passes the SOP 75 acceptance criteria score of <3 at 1 minute. The benzyl alcohol preserved foam (Formula 692-15-24 in FIG. 11) collapses in size (after 6 months storage, test at 30° C.) only approximately 30% after 1 minute, and passes the SOP 75 acceptance criteria score of <3 at 1 minute.

Concentration of Pramoxine HCl:

The two formulations of Example 18 show the storage stability at 40° C. as represented in Table 5.

TABLE 5

Pramoxine HCl (%) assay

| | Temperature (° C.) | Time Points | | | |
|---|---|---|---|---|---|
| | | 0 Month | 1 Month | 3 Month | 6 Month |
| w/w % (without Preservative) | 5 | 0.979 | 0.992 | 0.986 | 0.983 |
| | 25 | | 0.981 | | 0.982 |
| | 40 | | 0.989 | 0.977 | 0.977 |
| % w/w (with preservative) | 5 | 0.969 | 0.972 | 0.972 | 0.976 |
| | 40 | | 0.967 | 0.956 | 0.962 |

The unpreserved formulation exhibited 0.2% loss (compared to initial assay) after 6 months' storage at 40° C., hence is expected to meet a shelf life/expiry date of at least 24 months. The preserved formulation exhibited 0.7% loss (compared to initial assay) after 6 months' storage at 40° C., hence is expected to meet a shelf life/expiry date of at least 24 months.

pH Stability:

The pH drift with time in the two formulations of Example 18 was tested and the results are represented in Table 6.

TABLE 6 pH of foam

| | Temperature (° C.) | Time Points | | | |
|---|---|---|---|---|---|
| | | 0 Month | 1 Month | 3 Month | 6 Month |
| w/w % (without Preservative) | 5 | | | 4.57 | 4.63 |
| | 25 | 4.51 | | 4.55 | 4.59 |
| | 40 | | 4.53 | 4.56 | 4.58 |
| % w/w (with preservative) | 5 | | | 4.65 | 4.70 |
| | 40 | | | 4.63 | 4.70 |

A pH range of 4.75±0.25 has been identified as acceptable for 1% pramoxine HCl foam's physical, chemical and packaging stability. Table 6 shows that as the test progressed there was no significant drift in the pH of the foam expelled from the can.

In conclusion it will be appreciated that the process of the invention allows the formation of a stable oil-in-water microemulsion or sub-micron emulsion which allows for the inclusion of a hydrocarbon propellant so that a foam may be dispensed when the resulting product is in use. Moreover, the resultant foam appears stable and effective. It will be appreciated that the scope of the invention described herein is not limited to the specific embodiments described herein in the examples but extends to the general principles of the invention as set out in the summary and detailed description of the invention hereinabove.

The invention claimed is:

1. A process for the preparation of an oil in water (O/W) microemulsion or sub-micron emulsion composition for dermal delivery of at least one pharmaceutically active ingredient, the method comprising the successive steps of:
   a) admixing a first part comprising at least one selected from the group consisting of an animal oil, a mineral oil, a vegetable oil, a silane, a siloxane, an ester, a fatty acid, a fat, a halogen compound, and an alkoxylated alcohol; and at least one lipophilic surfactant, and
   a second part comprising water and at least one hydrophilic surfactant to achieve homogeneity,
   b) heating the mix of step a) to a phase assembly temperature in the range of 40-99° C. with continuous mixing to obtain an oil in water microemulsion or sub-micron emulsion,
   c) allowing the microemulsion or sub-micron emulsion to cool, and
   d) adding a third part to the microemulsion or sub-micron emulsion at a temperature between 2° C. and the phase assembly temperature, the third part if necessary being premixed and heated until the components are dissolved and comprising a non-surfactant amphiphilic type compound, that is a water miscible organic solvent and a pharmaceutically active ingredient that is insoluble or only sparingly soluble in water,
   wherein the weight ratio of the at least one hydrophilic surfactant to the at least one lipophilic surfactant is approximately 9.0:1.0 to 2.0:3.0.

2. The process according to claim 1 wherein the second part is added in two aliquots.

3. The process according to claim 2 wherein of the two aliquots one is about 70% by weight of the second part and another is about 30% by weight of the second part.

4. The process according to claim 1 wherein the pharmaceutically active ingredient is one or more water insoluble compounds selected from the group consisting of corticosteroids, desonide, clobetasol, betamethasone, vitamin D analogues and vitamin A analogues.

5. The process according to claim 1 wherein an occlusive agent is present in the first part.

6. The process according to claim 5 wherein the occlusive agent is petrolatum.

7. A process for the preparation of an oil in water (O/W) microemulsion or sub-micron emulsion composition for dermal delivery of at least one pharmaceutically active ingredient, the method comprising the successive steps of:
   a) heating a first part comprising at least one selected from the group consisting of an animal oil, a mineral oil, a vegetable oil, a silane, a siloxane, an ester, a fatty acid, a fat, a halogen compound, and an alkoxylated alcohol; and at least one lipophilic surfactant to a temperature of 40-99° C., and mixing to homogeneity,
   b) heating a second part comprising water and at least one hydrophilic surfactant to a temperature of 40-99° C., and mixing to achieve homogeneity,
   c) adding the second part to the first part at a temperature of 40-99° C., with continuous mixing whereby a microemulsion or sub-micron emulsion is formed at a phase assembly temperature,
   d) allowing the microemulsion or sub-micron emulsion to cool, and
   e) adding a third part to the microemulsion or sub-micron emulsion at a temperature between room temperature and the phase assembly temperature the third part having been premixed, and if necessary heated until the components are dissolved and comprising a non-surfactant amphiphilic type compound, that is a water miscible organic solvent and a pharmaceutically active ingredient that is insoluble or only sparingly soluble in water,
   wherein the weight ratio of the at least one hydrophilic surfactant to the at least one lipophilic surfactant is approximately 9.0:1.0 to 2.0:3.0.

8. The process according to claim 3 wherein the aliquot that is about 30% by weight of the second part is added after the microemulsion or sub-micron emulsion has formed, at a temperature below the temperature of the first aliquot, and at a rapid rate so as to reduce the overall temperature of the composition to below 60° C. whereby the microemulsion or sub-micron emulsion structure is fixed.

9. The process according to claim 7 wherein the second part is added in two aliquots.

10. The process according to claim 9 wherein of the two aliquots one is about 70% by weight of the second part and another is about 30% by weight of the second part.

11. The process according to claim 10 wherein the aliquot that is about 30% by weight of the second part is added after the microemulsion or sub-micron emulsion has formed, at a temperature below the temperature of the first aliquot, and at a rapid rate so as to reduce the overall temperature of the composition to below 60° C. whereby the microemulsion or sub-micron emulsion structure is fixed.

12. The process according to claim 7 wherein the pharmaceutically active ingredient is one or more water insoluble compounds selected from the group consisting of corticosteroids, desonide, clobetasol, betamethasone, vitamin D analogues and vitamin A analogues.

13. The process according to claim 7 wherein an occlusive agent is present in the first part.

14. The process according to claim 13 wherein the occlusive agent is petrolatum.

\* \* \* \* \*